United States Patent [19]
Daub et al.

[11] Patent Number: 6,063,987
[45] Date of Patent: May 16, 2000

[54] ISOLATED GENES AND PROTEINS ENCODING RESISTANCE TO PHOTOSENSITIZERS

[75] Inventors: Margaret E. Daub, Raleigh; Marilyn Ehrenshaft, Cary; Anne E. Jenns, Raleigh, all of N.C.

[73] Assignee: North Carolina State University, Raleigh, N.C.

[21] Appl. No.: 09/039,859

[22] Filed: Mar. 16, 1998

[51] Int. Cl.$^7$ .............................. C12N 5/04; C12N 15/29; C12N 15/82; A01H 5/00; A01H 5/10
[52] U.S. Cl. ..................... 800/279; 536/23.6; 435/69.1; 435/410; 435/419; 800/279; 800/317.3
[58] Field of Search ..................... 536/23.6; 435/69.1, 435/410, 419; 800/279, 278, 317.3

[56] References Cited

U.S. PATENT DOCUMENTS 5,262,306  11/1993  Robeson et al. .......................... 435/29

FOREIGN PATENT DOCUMENTS

WO 91/0506  4/1991  WIPO .

OTHER PUBLICATIONS

Napoli et al. The Plant Cell. 1989. vol. 2: 278–289.
Linthorst et al. Plant Cell. 1989. vol. 1: 285–291.
Carvalho et al. The EMBO J. 1992. vol. 11: 2995–2602.
Wliiamson et al. Trends of Microbiology. vol. 1993. vol. 1" 239–245.
Gupta et al. The Proc. Natl. Acad. Sci. 1993. vol. 90: 1629–1633.
Wu et al. 1995. The Plant Cell. 1995. vol. 7: 1357–1368.
Ehrenshaft, Jenns and Daub; Isolation of genes encoding resistance to the photactivated toxin cercosporin; *Phytopathology* 86(Supplement):S11(Abstract 93A) (Nov. 1996).
Ehrenshaft, Jenns and Daub; Characterization of gene involved in singlet oxygen resistance in *Cercospora nicotianae*; Poster Presentation, 19$^{th}$ Fungal Genetics Conference, Mar. 19–23 1997 at Asilomar, Pacific Grove, California.
Batchvarova et al., Cellular resistance in rice to cercosporin, a toxin of Cercospora; *Phytopathology* 82:642–646 (1992).
Braun et al., Mutations in the maize mitochondrial T–urf 13 gene eliminate sensitivity to a fungal pathotoxin; *PNAS USA* 86:4435–39 (1989).
Braun et al.; A Stationary–Phase Gene in *Saccharomyces cerevisiae* Is a Member of a Novel, Highly Conserved Gene Family; *J. Bacteriol* 178(23):6865 (1996).
Daub, A resistance of fungi to the photosensitizing toxin cercosporin; *Phytopathology* 77:1515–20 (1987).
Daub, Jenns and Ehrenshaft; Fungal resistance to photosensitizers that generate singlet oxygen; *Light Activated Pest Control*, American Chemical Society Press, Washington DC (1995); pp. 201–206 in JR Heitz and KR Downum, eds.
Daub et al.; Reductive detoxification as a mechanism of fungal resistance to singlet–oxygen–generating photosensitizers; *PNAS USA* 89:9588–92 (1992).
Daub and Payne; TheRole of Carotenoids in Resistance of Fungi to Cercosporin; *Phytopathology* 79:180–185 (1989).

Ehrenshaft, Jenns & Daub, Targeted Gene Disruption of Carotenoid Biosynthesis in *Cercospora nicotianae* reveals no role for carotenoids in photosensitizer resistance; *Molec Plant Microbe Interact*; 8:569–575 (1995).
Ehrenshaft and Upchurch; Isolation of light–enhanced cDNA clones of *Cercospora kikuchii*; *Appl. Environ. Microbiol.* 57:2671–2676 (1991).
Jenns and Daub; Characterization of mutants of *Cercospora nicotianae* sensitive to the toxin cercosporin; *Phytopathology* 85:906–912 (1995).
Ehrenshaft et al.; SORI, a Gene Required for Photosensitizer and Singlet Oxygen Resistance in Cercospora Fungi, is Highly Conserved in Divergent Organisms. *Molecular Cell* 1:603–609 (1998).
Jenns et al.; Isolation of mutants of the fungus *Cercospora nicotianae* altered in their response to singlet–oxygen–generating photosensitizers *Photochem. Photobiol.* 61:488–493 (1995).
Sivasubramaniam et al.; *Plant Mol. Biol.* 29:173–178 (1995).
Braun et al.; A Stationary–Phase Gene In *Saccharomyces cerevisiae* Is a Member of a Novel, Highly Conserved Gene Family; *Journal of Biotechnology* 178:68656872 (Dec. 1996).
Fillatti, J.J. et al.; Efficient Transfer of a Glyphosate Tolerance Gene Into Tomato Using A Binary Agrobacterium Tumefaciens Vector *Biotechnology* 5:726–730 (1987).
Fromm, M. E. et al.; Inheritance and Expresssion of Chimeric Genes in the Progeny of Transgenic Maize Plants *Biotechnology* 8:833–839 (1990).
Ehrenshaft, M. et al.; Isolation of genes encoding resistance to the photoactivated toxin cercosporin; *Phytopathology* 86(11 Suppl.) pg. S11 (1996(.
Timberlake, W.E.; Cloning and Analysis of Fungal Genes: More Gene Manipulations in Fungi; Edited by J.W. Bennett et al, San Diego: Academic Press, Inc.; pp. 51–58, (1991).
Copy of International Search Report PCT/US98/04981; International Search Report Mailing Date: Jul. 16, 1998.
Horsch et al.; A Simple and General Method for Transferring Genes into Plants, *Science* 227:1229–1230 (Mar. 8, 1985).
Tuveson et al.; Role of Cloned Carotenoid Genes Expressed in *Escherichia coli* in Protecting against Inactivation by Near–UV Light and Specific Phototoxic Molecules, *Journal of Bacteriology* 170:4675–4680 (Oct. 1988).
Woloshuk et al.; Genetic Transformation System for the Aflatoxin–Producing *Fungus Aspergillus flavus*, Applied *and Environmental Microbiology* 55:86–90 (Jan. 1989).

*Primary Examiner*—Lynette R. F. Smith
*Assistant Examiner*—Ousama Zaghmout
*Attorney, Agent, or Firm*—Myers Bigel Sibley & Sajovec

[57] ABSTRACT

The present invention is drawn to methods and compounds for providing resistance to photosensitizers in cells and organisms that are sensitive to photosensitizers. Specifically, an isolated nucleic acid molecule, which upon expression provides resistance to a photosensitizer, is described. Also described are methods of transforming cells and organisms with the isolated nucleic acid molecule, such that resistance to a photosensitizer is increased or provided to the cells and organisms so transformed.

42 Claims, 5 Drawing Sheets

```
GGATCCAAAA TTGGGCCATG TTGTGCAGAG TGCGGTCTGG GAGGGTAGAG TGTTTTCGGT
GTCAAGCTTC ACTCACGCAG GAGGTCAAAG TCTACACAGA AGACCTCATC GAGCAGCTGA
GCTCTCTTAT TGCGATTACA GCTCAGCACT CGGCCGAGGA ACGCGTGGAT TCCTGGTTCC
CCTCATGGGC ATTGTAGCTT CAGCAGACTC GTCCGCCGCG ACTCTGCTCG CGTATGAGTA
GCTCGTGCTG ACCAGCAATC GCGGAGCTGA GCTGCAGTGC TCGCATCGCA GTCACAGAAG
GATGACCACC GTCTTGTAGC GCGGCGCACG CGGGCCAGCA CCTGAGGTCG GAGGGTTGGC
ACATGGACGG ACGAGCTGGT GGTTGTCACA TGCCGGCTCA GTCGCGGCAC TCAGCAGGCA
GGGAAGGCGC CGTCGGACCC TGCAGCACGT CTCGGCTCCT TGGCCGAAGC ACGATCTTCC
CCGCGATCGC AGGCGCAAAT CACTCTTCGA ACATTTTCTC GCCGCATCTG GCCGCTGTCA
GAGGCAAGTC TCGCACCGTG TCGCGCCCTA CCAGACACAA GCACCCTCCT GTTCCAGTGC
TCGCCAAAGC ATTGCCGCAT CGAGCTTCCT TTCGCGACCA TTGCCTGCCC TCCGAGCCCA
GCATATAGAC TTTCCTAGTT CCGCCGATTT TCTTTCCAAG TGCCACCACC TCAATATCGC
CTTCGACTTT CTTTCACTGC TGCCCCGCCC TGCATCTGCA CGCCCCACCG CCATTGACCA
AATATAACAT CCTCCTACCC TCCGTCTCCA GCACCAGCTA GCACATGGCC TCTAACGGAA
CTTCTGTATC ACCTTTCCGA TCTCAAAAGA ACGCCGCAAT GGCTGTCAAC GACACCCCCG
CCAACGGCCA CGCCGAGCCC TCCACCATCA CCGCCGCCTC GAAGACCAAC ACCACGAAGA
TCACATCTCA GAATGATCCT CAGTCATCCT TCGCCGTCAA GGTCGGCTTG GCCCAGATGC
TCAAGGGTGG CGTGATCATG GATGTGGTCA ACGCAGAGCA AGCACGCATT GCTGAAGAGG
CGGGTGCATG TGCCGTCATG GCCCTCGAGC GTGTGCCAGC AGATATTCGA AAGGACGGTG
GCGTCGCTCG CATGAGCGAC CCACAAATGA TCAAGGACAT CATGAATGCT GTGACCATCC
CTGTCATGGC GAAGTCGAGG ATTGGTCACT TCGTGGAATG TCAGATTCTC CAAGCCATTG
GCGTGGACTA CATCGATGAG TCCGAGGTGC TCACACCTGC CGATCCAGTC AACCACATCG
ACAAGAGCGT TTACAATGTT CCATTCGTGT GTGGATGCAA GAACTTGGGT GAGGCCCTTC
GAAGAATATC AGAGGGCGCT GCCATGATCC GGACAAAGGG TGAAGCAGGA ACGGGAGATG
TCGTCGAGGC CGTGAGACAC ATGCAGACTG TCAATGCTGA GATCGCAAAG GCCAGCTCAG
CATCTGACGC TGATCTTCGC ATGATGGCAC GAGAGCTGCA GTGCGACTAC AACCTGCTCA
AGCAGACCGC ACAGCTCAAG AGACTGCCAG TGGTCAACTT CGCTGCAGGA GGTATCGCCA
CGCCGGCCGA CGCTGCCTTG ATGATGCAAA TGGGTTGCGA TGGTGTCTTC GTTGGATCTG
GTATCTTCAA GTCAGGCGAC GCGGCGAAGC GAGCAAAGGC CATTGTGCAG GCCACCACAC
ACTACAACGA CCCCAAGGTC CTGGCTGAGG TCAGCTCGGG TCTTGGTGAG GCAATGGTGG
GCATCAACTG CGACAAGCTG CCAGAGACAC AGAAGCTGGC GACCCGTGGC TGGTAGATGC
TGCAAATTCG AAAAAGAAAA CGGGAACATG ACTGTAGGCA TAGCAGCGGG CGCTTGGGTA
TGGGTGTGAT TGCAATCAAA AGAAAAGCGA GCGAGTTAGA GAGCACATCT GGGCGTGTTA
GATTCTGTAT CGCGCCTCAC CGCGCCTAGG
```

*FIGURE 1*

```
MASNGTSVSP FRSQKNAAMA VNDTPANGHA EPSTITAASK TNTTKITSQN DPQSSFAVKV
GLAQMLKGGV IMDVVNAEQA RIAEEAGACA VMALERVPAD IRKDGGVARM SDPQMIKDIM
NAVTIPVMAK SRIGHFVECQ ILQAIGVDYI DESEVLTPAD PVNHIDKSVY NVPFVCGCKN
LGEALRRISE GAAMIRTKGE AGTGDVVEAV RHMQTVNAEI AKASSASDAD LRMMARELQC
DYNLLKQTAQ LKRLPVVNFA AGGIATPADA ALMMQMGCDG VFVGSGIFKS GDAAKRAKAI
VQATTHYNDP KVLAEVSSGL GEAMVGINCD KLPETQKLAT RGW
```

*FIGURE 2*

```
          10         20         30         40         50
           |          |          |          |          |
  1  TATGCGCTGC TCAAGGAGAC GGCTAAGCTT GGTCGTCTGC CTGTTGTCAA

51  CTTTGCGGCG GGTGGTGTCG CAACACCCGC TGATGCTGCG TTGATGATGC

101  AGTTGGGTTG CGATGGTGTC TTTGTTGGTA GCGGTATCTT CAAGTCTGGA

151  GACGCAGCCA AGAGGGCCAA GGCCATCGTA CAGGCTGTTA CTCACTACAA

201  AGACCCCAAG GTGCTCATGG AAGTCAGCAT GGATTTGGGT GAGGCCATGG

251  TTGGTATCAA CTGCGGTACA ATGGGCGAGG AGGAGAAGCT TGCTAAGAGG

301  GGATGGTAGA
```

| | |
|---|---|
| AA1T7 | TATGCGCTGCTCAA |
| | ==  ======== |
| CSG | TACAACCTGCTCAA |

```
AA1T7    51- GGAGACGGCTAAGCTTGGTCGTCTGCCTGTTGTCAACTTTGCGGCGGGTG
             = ==== ==  ====     = ===== == ======== == == == =
CSG    1562- GCAGACCGCACAGCTCAAGAGACTGCCAGTGGTCAACTTCGCTGCAGGAG

AA1T7   101- GTGTCGCAACACCCGCTGATGCTGCGTTGATGATGCAGTTGGGTTGCGAT
             == ==== == == == == ===== ============  ===========
CSG    1612- GTATCGCCACGCCGGCCGACGCTGCCTTGATGATGCAAATGGGTTGCGAT

AA1T7   151- GGTGTCTTTGTTGGTAGC-GGTATCTTCAAGTCTGGAGACGCAGCCAAGA
             ======== ===== = = =============== == ===== == ===
CSG    1662- GGTGTCTTCGTTGG-ATCTGGTATCTTCAAGTCAGGCGACGCGGCGAAGC

AA1T7   200- GGGCCAAGGCCATCGTACAGGCTGTTACTCACTACAAAGACCCCAAGGTG
             = == ========= == =====    == ======== ============
CSG    1711- GAGCAAAGGCCATTGTGCAGGCCACCACACACTACAACGACCCCAAGGTC

AA1T7   250- CTCATGGAAGTCAGCATGGATTTGGGTGAGGCCATGGTTGGTATCAACTG
             ==     == ====== == = = ======== ===== == ========
CSG    1761- CTGGCTGAGGTCAGCTCGGGTCTTGGTGAGGCAATGGTGGGCATCAACTG

AA1T7   300- CGGTACAATGGGCGAG-GA-GGAGAAGCTTGCTAAGAGGGGATGGTAGA-
             = = ====  == == ==     ======== == =   = == =======
CSG    1811- C-G-ACAAGCTGCCAGAGACACAGAAGCTGGCGACCCGTGGCTGGTAGAT
```

FIGURE 4A

```
AAHOMOLOG -                                              LLKETAK  -   7
                                                         === ==
MAYBE2    - AGTGDVVEAVRHMQTVNAEIAKASSASDADLRMMARELQCDYNLLKQTAQ - 250

AAHOMOLOG - LGRLPVVNFAAGGVATPADAALMMQLGCDGVFVGSGIFKSGDAAKRAKAI -  57
            = ==========-============-==========================
MAYBE2    - LKRLPVVNFAAGGIATPADAALMMQMGCDGVFVGSGIFKSGDAAKRAKAI - 300

AAHOMOLOG - VQAVTHYKDPKVLMEVSMDLGEAMVGINCGTMGEEEKLAKRGW
            === === ===== ===  ==========  _  =  === ===
MAYBE2    - VQATTHYNDPKVLAEVSSGLGEAMVGINCDKLPETQKLATRGW        - 343
```

FIGURE 4B

```
C. nicot.  MASNGTSVSPFRSQKNAAMAVNDTPANGHAEPSTITAASKTNTTKITSQN - 50
           ==-   -                          -===-
Alt. alt.  MATELPT-----------------TNGHSAQ------------------ - 14

C. nicot.  DPQSSFAVKVGLAQMLKGGVIMDVVNAEQARIAEEAGACAVMALERVPAD - 100
           =     ====  ===  ===========================  ===========
Alt. alt.  DGENNFAVKAGLARMLKGGVIMDVVNAEQARIAEEAGASAVMALERVPAD - 64

C. nicot.  IRKDGGVARMSDPQMIKDIMNAVTIPVMAKSRIGHFVECQILQAIGVDYI - 150
           ==  ==========  ====-==  -=========-============ =-=====
Alt. alt.  IRSQGGVARMSDPKMIKEIMDTVTIPVMAKARIGHFVECQILEALGVDYI - 114

C. nicot.  DESEVLTPADPVNHIDKSVYNVPFVCGCKNLGEALRRISEGAAMIRTKGE - 200
           ==========  -  =-  =   -  -=======-  ====================
Alt. alt.  DESEVLTPADAIHHVSKHPFRIPFVCGCRGLGEALRRISEGAAMIRTKGE - 164

C. nicot.  AGTGDVVEAVRHMQTVNAEIAKASSASDADLRMMARELQCDYNLLKQTAQ - 250
           ======-======  ===-===-=  =  =-  -==-  =-===  ==  ===  ==
Alt. alt.  AGTGDVIEAVRHMRTVNSEIARAKSMSEEELRVYAKELQVDYALLKETAK - 214

C. nicot.  LKRLPVVNFAAGGIATPADAALMMQMGCDGVFVGSGIFKSGDAAKRAKAI - 300
           =  ============-==========  -==========================
Alt. alt.  LGRLPVVNFAAGGVATPADAALMMQLGCDGVFVGSGIFKSGDAAKRAKAI - 264

C. nicot.  VQATTHYNDPKVLAEVSSGLGEAMVGINCDKLPETQKLATRGW - 343
           ===  ===  =====  ===  ==========  -  =  ===  ===
Alt. alt.  VQAVTHYKDPKVLMEVSMDLGEAMVGINCGTMGEEEKLAKRGW - 307
```

FIGURE 4C

```
                            SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 2010 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 825..1853

(xi) SEQUENCE DESCRIPTION: SEQ ID NO:1:

GGATCCAAAA TTGGGCCATG TTGTGCAGAG TGCGGTCTGG GAGGGTAGAG TGTTTTCGGT      60

GTCAAGCTTC ACTCACGCAG GAGGTCAAAG TCTACACAGA AGACCTCATC GAGCAGCTGA     120

GCTCTCTTAT TGCGATTACA GCTCAGCACT CGGCCGAGGA ACGCGTGGAT TCCTGGTTCC     180

CCTCATGGGC ATTGTAGCTT CAGCAGACTC GTCCGCCGCG ACTCTGCTCG CGTATGAGTA     240

GCTCGTGCTG ACCAGCAATC GCGGAGCTGA GCTGCAGTGC TCGCATCGCA GTCACAGAAG     300

GATGACCACC GTCTTGTAGC GCGGCGCACG CGGGCCAGCA CCTGAGGTCG GAGGGTTGGC     360

ACATGGACGG ACGAGCTGGT GGTTGTCACA TGCCGGCTCA GTCGCGGCAC TCAGCAGGCA     420

GGGAAGGCGC CGTCGGACCC TGCAGCACGT CTCGGCTCCT TGGCCGAAGC ACGATCTTCC     480

CCGCGATCGC AGGCGCAAAT GACTCTTCGA ACATTTTCTC GCCGCATCTG GCCGCTGTCA     540

GAGGCAAGTC TCGCACCGTG TCGCGCCCTA CCAGACACAA GCACCCTCCT GTTCCAGTGC     600

TCGCCAAAGC ATTGCCGCAT CGAGCTTCCT TTCGCGACCA TTGCCTGCCC TCCGAGCCCA     660

GCATATAGAC TTTCCTAGTT CCGCCGATTT TCTTTCCAAG TGCCACCACC TCAATATCGC     720

CTTCGACTTT CTTTCACTGC TGCCCCGCCC TGCATCTGCA CGCCCCACCG CCATTGACCA     780

AATATAACAT CCTCCTACCC TCCGTCTCCA GCACCAGCTA GCAC ATG GCC TCT AAC     836
                                                 Met Ala Ser Asn
```

-continued

1

| | | | | | | | | | | | | | | | | |
|---|---|---|---|---|---|---|---|---|---|---|---|---|---|---|---|---|
| GGA | ACT | TCT | GTA | TCA | CCT | TTC | CGA | TCT | CAA | AAG | AAC | GCC | GCA | ATG | GCT | 884 |
| Gly | Thr | Ser | Val | Ser | Pro | Phe | Arg | Ser | Gln | Lys | Asn | Ala | Ala | Met | Ala | |
| 5 | | | | 10 | | | | | 15 | | | | | 20 | | |
| GTC | AAC | GAC | ACC | CCC | GCC | AAC | GGC | CAC | GCC | GAG | CCC | TCC | ACC | ATC | ACC | 932 |
| Val | Asn | Asp | Thr | Pro | Ala | Asn | Gly | His | Ala | Glu | Pro | Ser | Thr | Ile | Thr | |
| | | | 25 | | | | | 30 | | | | | 35 | | | |
| GCC | GCC | TCG | AAG | ACC | AAC | ACC | ACG | AAG | ATC | ACA | TCT | CAG | AAT | GAT | CCT | 980 |
| Ala | Ala | Ser | Lys | Thr | Asn | Thr | Thr | Lys | Ile | Thr | Ser | Gln | Asn | Asp | Pro | |
| | | | 40 | | | | | 45 | | | | | 50 | | | |
| CAG | TCA | TCC | TTC | GCC | GTC | AAG | GTC | GGC | TTG | GCC | CAG | ATG | CTC | AAG | GGT | 1028 |
| Gln | Ser | Ser | Phe | Ala | Val | Lys | Val | Gly | Leu | Ala | Gln | Met | Leu | Lys | Gly | |
| | | 55 | | | | | 60 | | | | | 65 | | | | |
| GGC | GTG | ATC | ATG | GAT | GTG | GTC | AAC | GCA | GAG | CAA | GCA | CGC | ATT | GCT | GAA | 1076 |
| Gly | Val | Ile | Met | Asp | Val | Val | Asn | Ala | Glu | Gln | Ala | Arg | Ile | Ala | Glu | |
| | 70 | | | | | 75 | | | | | 80 | | | | | |
| GAG | GCG | GGT | GCA | TGT | GCC | GTC | ATG | GCC | CTC | GAG | CGT | GTG | CCA | GCA | GAT | 1124 |
| Glu | Ala | Gly | Ala | Cys | Ala | Val | Met | Ala | Leu | Glu | Arg | Val | Pro | Ala | Asp | |
| 85 | | | | | 90 | | | | | 95 | | | | | 100 | |
| ATT | CGA | AAG | GAC | GGT | GGC | GTC | GCT | CGC | ATG | AGC | GAC | CCA | CAA | ATG | ATC | 1172 |
| Ile | Arg | Lys | Asp | Gly | Gly | Val | Ala | Arg | Met | Ser | Asp | Pro | Gln | Met | Ile | |
| | | | | 105 | | | | | 110 | | | | | 115 | | |
| AAG | GAC | ATC | ATG | AAT | GCT | GTG | ACC | ATC | CCT | GTC | ATG | GCG | AAG | TCG | AGG | 1220 |
| Lys | Asp | Ile | Met | Asn | Ala | Val | Thr | Ile | Pro | Val | Met | Ala | Lys | Ser | Arg | |
| | | | 120 | | | | | 125 | | | | | 130 | | | |
| ATT | GGT | CAC | TTC | GTG | GAA | TGT | CAG | ATT | CTC | CAA | GCC | ATT | GGC | GTG | GAC | 1268 |
| Ile | Gly | His | Phe | Val | Glu | Cys | Gln | Ile | Leu | Gln | Ala | Ile | Gly | Val | Asp | |
| | | 135 | | | | | 140 | | | | | 145 | | | | |
| TAC | ATC | GAT | GAG | TCC | GAG | GTG | CTC | ACA | CCT | GCC | GAT | CCA | GTC | AAC | CAC | 1316 |
| Tyr | Ile | Asp | Glu | Ser | Glu | Val | Leu | Thr | Pro | Ala | Asp | Pro | Val | Asn | His | |
| | 150 | | | | | 155 | | | | | 160 | | | | | |
| ATC | GAC | AAG | AGC | GTT | TAC | AAT | GTT | CCA | TTC | GTG | TGT | GGA | TGC | AAG | AAC | 1364 |
| Ile | Asp | Lys | Ser | Val | Tyr | Asn | Val | Pro | Phe | Val | Cys | Gly | Cys | Lys | Asn | |
| 165 | | | | | 170 | | | | | 175 | | | | | 180 | |
| TTG | GGT | GAG | GCC | CTT | CGA | AGA | ATA | TCA | GAG | GGC | GCT | GCC | ATG | ATC | CGG | 1412 |
| Leu | Gly | Glu | Ala | Leu | Arg | Arg | Ile | Ser | Glu | Gly | Ala | Ala | Met | Ile | Arg | |
| | | | | 185 | | | | | 190 | | | | | 195 | | |
| ACA | AAG | GGT | GAA | GCA | GGA | ACG | GGA | GAT | GTC | GTC | GAG | GCC | GTG | AGA | CAC | 1460 |
| Thr | Lys | Gly | Glu | Ala | Gly | Thr | Gly | Asp | Val | Val | Glu | Ala | Val | Arg | His | |
| | | | 200 | | | | | 205 | | | | | 210 | | | |
| ATG | CAG | ACT | GTC | AAT | GCT | GAG | ATC | GCA | AAG | GCC | AGC | TCA | GCA | TCT | GAC | 1508 |
| Met | Gln | Thr | Val | Asn | Ala | Glu | Ile | Ala | Lys | Ala | Ser | Ser | Ala | Ser | Asp | |
| | | 215 | | | | | 220 | | | | | 225 | | | | |
| GCT | GAT | CTT | CGC | ATG | ATG | GCA | CGA | GAG | CTG | CAG | TGC | GAC | TAC | AAC | CTG | 1556 |
| Ala | Asp | Leu | Arg | Met | Met | Ala | Arg | Glu | Leu | Gln | Cys | Asp | Tyr | Asn | Leu | |
| | 230 | | | | | 235 | | | | | 240 | | | | | |
| CTC | AAG | CAG | ACC | GCA | CAG | CTC | AAG | AGA | CTG | CCA | GTG | GTC | AAC | TTC | GCT | 1604 |
| Leu | Lys | Gln | Thr | Ala | Gln | Leu | Lys | Arg | Leu | Pro | Val | Val | Asn | Phe | Ala | |
| 245 | | | | | 250 | | | | | 255 | | | | | 260 | |
| GCA | GGA | GGT | ATC | GCC | ACG | CCG | GCC | GAC | GCT | GCC | TTG | ATG | ATG | CAA | ATG | 1652 |
| Ala | Gly | Gly | Ile | Ala | Thr | Pro | Ala | Asp | Ala | Ala | Leu | Met | Met | Gln | Met | |
| | | | | 265 | | | | | 270 | | | | | 275 | | |
| GGT | TGC | GAT | GGT | GTC | TTC | GTT | GGA | TCT | GGT | ATC | TTC | AAG | TCA | GGC | GAC | 1700 |
| Gly | Cys | Asp | Gly | Val | Phe | Val | Gly | Ser | Gly | Ile | Phe | Lys | Ser | Gly | Asp | |
| | | | 280 | | | | | 285 | | | | | 290 | | | |
| GCG | GCG | AAG | CGA | GCA | AAG | GCC | ATT | GTG | CAG | GCC | ACC | ACA | CAC | TAC | AAC | 1748 |
| Ala | Ala | Lys | Arg | Ala | Lys | Ala | Ile | Val | Gln | Ala | Thr | Thr | His | Tyr | Asn | |
| | | 295 | | | | | 300 | | | | | 305 | | | | |
| GAC | CCC | AAG | GTC | CTG | GCT | GAG | GTC | AGC | TCG | GGT | CTT | GGT | GAG | GCA | ATG | 1796 |

```
Asp Pro Lys Val Leu Ala Glu Val Ser Ser Gly Leu Gly Glu Ala Met
    310                 315                 320
```

```
GTG GGC ATC AAC TGC GAC AAG CTG CCA GAG ACA CAG AAG CTG GCG ACC     1844
Val Gly Ile Asn Cys Asp Lys Leu Pro Glu Thr Gln Lys Leu Ala Thr
325             330                 335                 340
```

```
CGT GGC TGG TAGATGCTGC AAATTCGAAA AGAAAACGG GAACATGACT              1893
Arg Gly Trp
```

```
GTAGGCATAG CAGCGGGCGC TTGGGTATGG GTGTGATTGC AATCAAAAGA AAAGCGAGCG   1953
```

```
AGTTAGAGAG CACATCTGGG CGTGTTAGAT TCTGTATCGC GCCTCACCGC GCCTAGG      2010
```

(2) INFORMATION FOR SEQ ID NO:2:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Asn Gly Thr Ser Val Ser Pro Phe Arg Ser Gln Lys Asn
 1               5                  10                  15

Ala Ala Met Ala Val Asn Asp Thr Pro Ala Asn Gly His Ala Glu Pro
            20                  25                  30

Ser Thr Ile Thr Ala Ala Ser Lys Thr Asn Thr Thr Lys Ile Thr Ser
        35                  40                  45

Gln Asn Asp Pro Gln Ser Ser Phe Ala Val Lys Val Gly Leu Ala Gln
    50                  55                  60

Met Leu Lys Gly Gly Val Ile Met Asp Val Val Asn Ala Glu Gln Ala
65                  70                  75                  80

Arg Ile Ala Glu Glu Ala Gly Ala Cys Ala Val Met Ala Leu Glu Arg
                85                  90                  95

Val Pro Ala Asp Ile Arg Lys Asp Gly Gly Val Ala Arg Met Ser Asp
                100                 105                 110

Pro Gln Met Ile Lys Asp Ile Met Asn Ala Val Thr Ile Pro Val Met
            115                 120                 125

Ala Lys Ser Arg Ile Gly His Phe Val Glu Cys Gln Ile Leu Gln Ala
    130                 135                 140

Ile Gly Val Asp Tyr Ile Asp Glu Ser Glu Val Leu Thr Pro Ala Asp
145                 150                 155                 160

Pro Val Asn His Ile Asp Lys Ser Val Tyr Asn Val Pro Phe Val Cys
                165                 170                 175

Gly Cys Lys Asn Leu Gly Glu Ala Leu Arg Arg Ile Ser Glu Gly Ala
                180                 185                 190

Ala Met Ile Arg Thr Lys Gly Glu Ala Gly Thr Gly Asp Val Val Glu
            195                 200                 205

Ala Val Arg His Met Gln Thr Val Asn Ala Glu Ile Ala Lys Ala Ser
    210                 215                 220

Ser Ala Ser Asp Ala Asp Leu Arg Met Met Ala Arg Glu Leu Gln Cys
225                 230                 235                 240

Asp Tyr Asn Leu Leu Lys Gln Thr Ala Gln Leu Lys Arg Leu Pro Val
                245                 250                 255

Val Asn Phe Ala Ala Gly Gly Ile Ala Thr Pro Ala Asp Ala Ala Leu
                260                 265                 270

Met Met Gln Met Gly Cys Asp Gly Val Phe Val Gly Ser Gly Ile Phe
            275                 280                 285
```

```
Lys Ser Gly Asp Ala Ala Lys Arg Ala Lys Ala Ile Val Gln Ala Thr
    290                 295                 300

Thr His Tyr Asn Asp Pro Lys Val Leu Ala Glu Val Ser Ser Gly Leu
305                 310                 315                 320

Gly Glu Ala Met Val Gly Ile Asn Cys Asp Lys Leu Pro Glu Thr Gln
                325                 330                 335

Lys Leu Ala Thr Arg Gly Trp
            340
```

(2) INFORMATION FOR SEQ ID NO:3:

(i) SEQUENCE CHARACTERISTICS:
        (A) LENGTH: 310 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TATGCGCTGC TCAAGGAGAC GGCTAAGCTT GGTCGTCTGC CTGTTGTCAA CTTTGCGGCG    60

GGTGGTGTCG CAACACCCGC TGATGCTGCG TTGATGATGC AGTTGGGTTG CGATGGTGTC   120

TTTGTTGGTA GCGGTATCTT CAAGTCTGGA GACGCAGCCA AGAGGGCCAA GGCCATCGTA   180

CAGGCTGTTA CTCACTACAA AGACCCCAAG GTGCTCATGG AAGTCAGCAT GGATTTGGGT   240

GAGGCCATGG TTGGTATCAA CTGCGGTACA ATGGGCGAGG AGGAGAAGCT TGCTAAGAGG   300

GGATGGTAGA                                                         310
```

(2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:4:

```
Tyr Ala Leu Leu Lys Glu Thr Ala Lys Leu Gly Arg Leu Pro Val Val
1               5                   10                  15

Asn Phe Ala Ala Gly Gly Val Ala Thr Pro Ala Asp Ala Ala Leu Met
            20                  25                  30

Met Gln Leu Gly Cys Asp Gly Val Phe Val Gly Ser Gly Ile Phe Lys
        35                  40                  45

Ser Gly Asp Ala Ala Lys Arg Ala Lys Ala Ile Val Gln Ala Thr
    50                  55                  60

His Tyr Lys Asp Pro Lys Val Leu Met Glu Val Ser Met Asp Leu Gly
65                  70                  75                  80

Glu Ala Met Val Gly Ile Asn Cys Gly Thr Met Gly Glu Glu Glu Lys
                85                  90                  95

Leu Ala Lys Arg Gly Trp
            100
```

(2) INFORMATION FOR SEQ ID NO:5:

(i) SEQUENCE CHARACTERISTICS:
        (A) LENGTH: 311 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:5:

```
TACAACCTGC TCAAGCAGAC CGCACAGCTC AAGAGACTGC CAGTGGTCAA CTTCGCTGCA      60

GGAGGTATCG CCACGCCGGC CGACGCTGCC TTGATGATGC AAATGGGTTG CGATGGTGTC     120

TTCGTTGGAT CTGGTATCTT CAAGTCAGGC GACGCGGCGA AGCGAGCAAA GGCCATTGTG     180

CAGGCCACCA CACACTACAA CGACCCCAAG GTCCTGGCTG AGGTCAGCTC GGGTCTTGGT     240

GAGGCAATGG TGGGCATCAA CTGCGACAAG CTGCCAGAGA CACAGAAGCT GGCGACCCGT     300

GGCTGGTAGA T                                                         311
```

(2) INFORMATION FOR SEQ ID NO:6:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu Leu Lys Glu Thr Ala Lys Leu Gly Arg Leu Pro Val Val Asn Phe
1               5                   10                  15

Ala Ala Gly Gly Val Ala Thr Pro Ala Asp Ala Ala Leu Met Met Gln
            20                  25                  30

Leu Gly Cys Asp Gly Val Phe Val Gly Ser Gly Ile Phe Lys Ser Gly
        35                  40                  45

Asp Ala Ala Lys Arg Ala Lys Ala Ile Val Gln Ala Val Thr His Tyr
    50                  55                  60

Lys Asp Pro Lys Val Leu Met Glu Val Ser Met Asp Leu Gly Glu Ala
65                  70                  75                  80

Met Val Gly Ile Asn Cys Gly Thr Met Gly Glu Glu Lys Leu Ala
                85                  90                  95

Lys Arg Gly Trp
            100
```

(2) INFORMATION FOR SEQ ID NO:7:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala Gly Thr Gly Asp Val Val Glu Ala Val Arg His Met Gln Thr Val
1               5                   10                  15

Asn Ala Glu Ile Ala Lys Ala Ser Ser Ala Ser Asp Ala Asp Leu Arg
            20                  25                  30

Met Met Ala Arg Glu Leu Gln Cys Asp Tyr Asn Leu Leu Lys Gln Thr
        35                  40                  45

Ala Gln Leu Lys Arg Leu Pro Val Val Asn Phe Ala Ala Gly Gly Ile
    50                  55                  60

Ala Thr Pro Ala Asp Ala Ala Leu Met Met Gln Met Gly Cys Asp Gly
65                  70                  75                  80
```

-continued

```
Val Phe Val Gly Ser Gly Ile Phe Lys Ser Gly Asp Ala Ala Lys Arg
             85                  90                  95

Ala Lys Ala Ile Val Gln Ala Thr Thr His Tyr Asn Asp Pro Lys Val
            100                 105                 110

Leu Ala Glu Val Ser Ser Gly Leu Gly Glu Ala Met Val Gly Ile Asn
        115                 120                 125

Cys Asp Lys Leu Pro Glu Thr Gln Lys Leu Ala Thr Arg Gly Trp
    130                 135                 140
```

(2) INFORMATION FOR SEQ ID NO:8:

(i) SEQUENCE CHARACTERISTICS:
        (A) LENGTH: 3420 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 742..2391

(xi) SEQUENCE DESCRIPTION: SEQ ID NO:8:

```
GGATCCCCGA TCCAGCGGGA GTATTTGACA TGATTAGGTT CCTTCGGCGA CTACATTGTG     60

AAGTGGTATG CTCGAAGGTC GCATTCCATT GCCATGTCTC TGCAGCGTAG CGTCGAATAC    120

AGCACTTGTT GGGAGAATTG CAGATAGGAG TACAGTCAAC TCAACTTCGA AACAAGTCGT    180

ACTGTACTGC TCAAAGAACC TCAGAGAAAG GTTTCCCACA AGTCTACAGG GATGATTACC    240

GGCATCTGAT TCGCTACCCA ATCGCGCTAT TCCACGTCTG AGCCTTAGCA TCAACTCACC    300

TCTCTCTCAC CCAAGACATT CTGTCACAGC CTCGCGGTGC TTTTTCCGTC ATGCCACATC    360

GCACTTTTCG ACGGCCATGT CACCACGAAT GCCGCAGAAA CGGGGCAGAG CCTGTGAGGC    420

TTGCTCAAAG ATCAAAATCC GGTGCGTGGT CATAACTTCC CGATCAATAG TGGTGCCTGC    480

CACGCGCTGA TGTGATCTGC ATCAAGGTGT TCGCTGGGCC AGGCATCAGA GGATGCAGCA    540

CCGCCTTGCG AGAGATGCGT GCGATTGAAC AAGGAATGCA TTTTGAGCGC TCCAAAGCGT    600

CAGAAAGACC GCGTCGCCGA ACTTGAAGCA CAAGTGGCAC AGTTGACACG ACTGCTTGAG    660

AGTCAGCATA TCCAAGTACC TTCCGTTTCT CCGGCTACGG CCTCACAAAG CAATCAAGAT    720

GAATCACCTA CACCCGCGCA G ATG GTA AGC GCG TCT GGA ACA GCG ACG AAG      771
                       Met Val Ser Ala Ser Gly Thr Ala Thr Lys
                         1               5                  10

AAG CGA CGA CTA GAC TCC GAT GGA GAA ACG CCG CAA TCG AGC GTA TCT     819
Lys Arg Arg Leu Asp Ser Asp Gly Glu Thr Pro Gln Ser Ser Val Ser
             15                  20                  25

TCA CCA GGC ACC CAG AAT CCA GAC ATC TCT GAC ATC CAA CGA CTT GAT     867
Ser Pro Gly Thr Gln Asn Pro Asp Ile Ser Asp Ile Gln Arg Leu Asp
         30                  35                  40

CGG GTA CTC TCC TAT GAG CTG CAA CAG CGA ACG CTG ACT CGC TAT GTC     915
Arg Val Leu Ser Tyr Glu Leu Gln Gln Arg Thr Leu Thr Arg Tyr Val
     45                  50                  55

ACC GAG ATA GCA CCA CTC TTC CCA GCA GTG CCA GCG CCA GCG GAT TGC     963
Thr Glu Ile Ala Pro Leu Phe Pro Ala Val Pro Ala Pro Ala Asp Cys
 60                  65                  70

TCG TTG CCC GAA ATG AGA GCG AAT CGA CCC ACG TTG CTT ATG GCT TTC    1011
Ser Leu Pro Glu Met Arg Ala Asn Arg Pro Thr Leu Leu Met Ala Phe
 75                  80                  85                  90

TTA TAT GCT GCC AGT TGC GGC TTT CTT TCG CTT GAT ACT CAA GAA GAT    1059
```

```
Leu Tyr Ala Ala Ser Cys Gly Phe Leu Ser Leu Asp Thr Gln Glu Asp
                 95                 100                 105

GTA GCT CAA ATT CTG CTC AAT ACC CTC TCT GCA AGA GCA ATC ACG CAC       1107
Val Ala Gln Ile Leu Leu Asn Thr Leu Ser Ala Arg Ala Ile Thr His
            110                 115                 120

GGA GAG GAG ACG CTT GAA TTG ATA CAA GCT ATT CAG ATT GCC TGC TTG       1155
Gly Glu Glu Thr Leu Glu Leu Ile Gln Ala Ile Gln Ile Ala Cys Leu
                125                 130                 135

TGG TAT CGC TCA CCG AAG CAC CAT CGA CGT GCG GCC GTC TAC CAG CTC       1203
Trp Tyr Arg Ser Pro Lys His His Arg Arg Ala Ala Val Tyr Gln Leu
    140                 145                 150

ATT GAC ATC GCT TCT GCC ATG GCC AAT GGT CTC AGC GCA GGC GGT CCA       1251
Ile Asp Ile Ala Ser Ala Met Ala Asn Gly Leu Ser Ala Gly Gly Pro
155                 160                 165                 170

CTC GCT CCT CCG ACC AAA GGA CTG ACT TTG GAC GAT TGC GCG GAT ACG       1299
Leu Ala Pro Pro Thr Lys Gly Leu Thr Leu Asp Asp Cys Ala Asp Thr
                175                 180                 185

GGG TCG TAC GAG TCG GTA GAG GGC TGG CGC GCC TGG CTT GGC TGC CAT       1347
Gly Ser Tyr Glu Ser Val Glu Gly Trp Arg Ala Trp Leu Gly Cys His
                190                 195                 200

GTA CTG TCT GTC TCT ATG GCC ATT TTC ATG AGG AAA TCG ATG ACT GCA       1395
Val Leu Ser Val Ser Met Ala Ile Phe Met Arg Lys Ser Met Thr Ala
            205                 210                 215

AGT TGG ACC GAA CAG CAC GAG CAG GCA CGT CTG ATG CTG CAG TAC TCG       1443
Ser Trp Thr Glu Gln His Glu Gln Ala Arg Leu Met Leu Gln Tyr Ser
    220                 225                 230

CCC TTG AAC GCA GAC TCT GAT AGG TGG CTT GCT CAG TAC ATC AGA GCC       1491
Pro Leu Asn Ala Asp Ser Asp Arg Trp Leu Ala Gln Tyr Ile Arg Ala
235                 240                 245                 250

GAG CGA CTA TGC GAA GAG GTT TCT GAA CAG GTG GAT TTG ACT AAC ACA       1539
Glu Arg Leu Cys Glu Glu Val Ser Glu Gln Val Asp Leu Thr Asn Thr
                255                 260                 265

TCT TTC TAT CGC GAC GTT GCT GAT CCT GCA ACA AGA AAT CCA GTG CAG       1587
Ser Phe Tyr Arg Asp Val Ala Asp Pro Ala Thr Arg Asn Pro Val Gln
                270                 275                 280

ACA TGT CGA AAC AAG ATT CTG AAT TGG AAA ATG GGT GTT CCG CAA AGG       1635
Thr Cys Arg Asn Lys Ile Leu Asn Trp Lys Met Gly Val Pro Gln Arg
            285                 290                 295

TTA CGC TCT CCG TTG ATC ATG TTC TGG GAA CAT GTA GCA ACA GCA TAC       1683
Leu Arg Ser Pro Leu Ile Met Phe Trp Glu His Val Ala Thr Ala Tyr
    300                 305                 310

ATG CAT GAA CCA GTC CTG CAC ACA GCA ACG AAC AAG GAC AGC TTT ACG       1731
Met His Glu Pro Val Leu His Thr Ala Thr Asn Lys Asp Ser Phe Thr
315                 320                 325                 330

GCA CCT TAT TTG GCA GAA AGG CTG TCA CTG ACA GAC TTT CCG ACT CCG       1779
Ala Pro Tyr Leu Ala Glu Arg Leu Ser Leu Thr Asp Phe Pro Thr Pro
                335                 340                 345

CTC GTC ACT CAA GAT CAC ATC ACA GCT GTG TAC GAG CTG ACT GCG GCT       1827
Leu Val Thr Gln Asp His Ile Thr Ala Val Tyr Glu Leu Thr Ala Ala
                350                 355                 360

GTA CAA GCC GTT CTG GAC ATC TTT ATC AAC TAC GAC ACT AAA TCT CTC       1875
Val Gln Ala Val Leu Asp Ile Phe Ile Asn Tyr Asp Thr Lys Ser Leu
            365                 370                 375

GTT GCC TCT CCG AGC TTG GTG TAT GCT GCC AGA GCT GCG TAT GCG CTC       1923
Val Ala Ser Pro Ser Leu Val Tyr Ala Ala Arg Ala Ala Tyr Ala Leu
    380                 385                 390

TAT GTT CTG GCG AAG CTA TAC ATC GCT GTC ACT GCA CCA GGA AAT ACA       1971
Tyr Val Leu Ala Lys Leu Tyr Ile Ala Val Thr Ala Pro Gly Asn Thr
395                 400                 405                 410
```

```
CTT GGC ACA ATT CTG GAC GCC AGT ATT CTT GCC CTG CCG GAG TAC GCT       2019
Leu Gly Thr Ile Leu Asp Ala Ser Ile Leu Ala Leu Pro Glu Tyr Ala
                415                 420                 425

GAC AGG CTG GCA ACA TGC GGC TCA CGA ATT AGA GCG CTC GAT GAG CGT       2067
Asp Arg Leu Ala Thr Cys Gly Ser Arg Ile Arg Ala Leu Asp Glu Arg
            430                 435                 440

TGC GGT CCG GCT CGA ATC ATG CAT TGC GCA CCG GCG ATC AAG GAC TGG       2115
Cys Gly Pro Ala Arg Ile Met His Cys Ala Pro Ala Ile Lys Asp Trp
        445                 450                 455

TAT CTG AAC TAT ACT CAA TTC CTC TCC TCG AAC GCT GCA CTC GCC CAG       2163
Tyr Leu Asn Tyr Thr Gln Phe Leu Ser Ser Asn Ala Ala Leu Ala Gln
    460                 465                 470

TCG ATC CAG GTC TCC AAC GAC AAT GTG GCG GAG GCT CAG ATG ACT TTG       2211
Ser Ile Gln Val Ser Asn Asp Asn Val Ala Glu Ala Gln Met Thr Leu
475                 480                 485                 490

CCG CCG CTC CAA GAC AAC ACG AAC GCA TTT AGC AAT ATT CCA CCG GAT       2259
Pro Pro Leu Gln Asp Asn Thr Asn Ala Phe Ser Asn Ile Pro Pro Asp
                495                 500                 505

TGG GAG AAT CTG CTC ATG TTC GGT GAT AGT TCC ACG GAC TAT GGC TTC       2307
Trp Glu Asn Leu Leu Met Phe Gly Asp Ser Ser Thr Asp Tyr Gly Phe
            510                 515                 520

GAT CAG CTG TTT GCT GAA CCT ATT CCT CTA CAG CTC GAG CAG CCC ATA       2355
Asp Gln Leu Phe Ala Glu Pro Ile Pro Leu Gln Leu Glu Gln Pro Ile
        525                 530                 535

TTT GCC AAT ACG ATA CCT ACT GCG TTT GCG ACG AAG TGATCCAACA            2401
Phe Ala Asn Thr Ile Pro Thr Ala Phe Ala Thr Lys
    540                 545                 550

CGCGGCAAGA CGGGATCTCT GCTGTCAACG AAGCAGCGCA TGAAGCTCCA GAATGGGGAT     2461

CACATACCGA CGTTACGTTC TTCTTGGGCG AAGAAGAAGA CTTGCATCAT CAGCGTACTG     2521

CATCGTCGAA GTCGGTGATC CACGAACAAA TCGATGGCTC GGCTCGCATG CCATCAATCC     2581

GAAAATTTGC GATGATTGGG CACACTCGTC TTTGCGGAGC TCTGCCATAA GTCGCGCTTG     2641

GAAGACTTCG TGGCAACGAT CGATGCGTCA GCTGCAGAAA GGCCGGTTCT TTGAATTGCC     2701

GTGTTAGCAG AGGCAGTACT GAACAAGTCC GCACCCTTAG ATGTCTGCAT CCTGCAAAAT     2761

GGCGAATGTC CGATCAGAGC TCGACAAAAA TTGTCAATGG GGTCTTGAGG TGTGCCCATA     2821

TTGAGGAGCG ATGGAAGACC GCACGTCTGC GAAGTCGTCT GTGGATGAAG AAGTCTGCAT     2881

TCTGCGCATG TAACCTCGTA CATGTGCACT GTCGGAAATA GCTGGAGCAA GTGGGCTAAG     2941

GTTACCCGAA GTGGAACATT AGCCAAGCTC CATCGGCGCG ATTGCTCGAT GTTATCGAGT     3001

CATGGAAACC AGGATGACAG TCCCGCGCCA GCGCCGCCCA CGTGCAACTA TCAGACTATC     3061

TATCTCAGTG CTATCTACTG ATAAGCACGA GGGATCACGA CGAACGGAAT CGACAGCGAT     3121

GACCATGAAA AGCTGCCGGA CACATGGGTT CACATCATTC ATCTGCAGTT GTGAAAACCT     3181

TTCGCCTGCA CATCAGTCCA TCGGTTGTGG GGTCTCGCGA CATGCAATTC TTTATAATAA     3241

GTACTGTTCG TCCACATGAG TGACGCGATA CAAGTGGCCA GCAGAGCCTG CTGTCAAATC     3301

CCTGTTTCGT CACCGGACGA TCACGGGCGC TGCTCAGAAT CAACACCTTT GCTTCAAGAC     3361

TCAATGTCCT CGGGTGGTCA TCGCAATATG TCGTCCAGCA TGGAGAAATT CAAGAATTC      3420
```

(2) INFORMATION FOR SEQ ID NO:9:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:9:

```
Met Val Ser Ala Ser Gly Thr Ala Thr Lys Lys Arg Arg Leu Asp Ser
  1               5                  10                  15

Asp Gly Glu Thr Pro Gln Ser Ser Val Ser Ser Pro Gly Thr Gln Asn
                 20                  25                  30

Pro Asp Ile Ser Asp Ile Gln Arg Leu Asp Arg Val Leu Ser Tyr Glu
                 35                  40                  45

Leu Gln Gln Arg Thr Leu Thr Arg Tyr Val Thr Glu Ile Ala Pro Leu
         50                  55                  60

Phe Pro Ala Val Pro Ala Pro Ala Asp Cys Ser Leu Pro Glu Met Arg
 65                  70                  75                  80

Ala Asn Arg Pro Thr Leu Leu Met Ala Phe Leu Tyr Ala Ala Ser Cys
                 85                  90                  95

Gly Phe Leu Ser Leu Asp Thr Gln Glu Asp Val Ala Gln Ile Leu Leu
                100                 105                 110

Asn Thr Leu Ser Ala Arg Ala Ile Thr His Gly Glu Glu Thr Leu Glu
                115                 120                 125

Leu Ile Gln Ala Ile Gln Ile Ala Cys Leu Trp Tyr Arg Ser Pro Lys
        130                 135                 140

His His Arg Arg Ala Ala Val Tyr Gln Leu Ile Asp Ile Ala Ser Ala
145                 150                 155                 160

Met Ala Asn Gly Leu Ser Ala Gly Gly Pro Leu Ala Pro Pro Thr Lys
                165                 170                 175

Gly Leu Thr Leu Asp Asp Cys Ala Asp Thr Gly Ser Tyr Glu Ser Val
                180                 185                 190

Glu Gly Trp Arg Ala Trp Leu Gly Cys His Val Leu Ser Val Ser Met
        195                 200                 205

Ala Ile Phe Met Arg Lys Ser Met Thr Ala Ser Trp Thr Glu Gln His
        210                 215                 220

Glu Gln Ala Arg Leu Met Leu Gln Tyr Ser Pro Leu Asn Ala Asp Ser
225                 230                 235                 240

Asp Arg Trp Leu Ala Gln Tyr Ile Arg Ala Glu Arg Leu Cys Glu Glu
                245                 250                 255

Val Ser Glu Gln Val Asp Leu Thr Asn Thr Ser Phe Tyr Arg Asp Val
                260                 265                 270

Ala Asp Pro Ala Thr Arg Asn Pro Val Gln Thr Cys Arg Asn Lys Ile
                275                 280                 285

Leu Asn Trp Lys Met Gly Val Pro Gln Arg Leu Arg Ser Pro Leu Ile
        290                 295                 300

Met Phe Trp Glu His Val Ala Thr Ala Tyr Met His Glu Pro Val Leu
305                 310                 315                 320

His Thr Ala Thr Asn Lys Asp Ser Phe Thr Ala Pro Tyr Leu Ala Glu
                325                 330                 335

Arg Leu Ser Leu Thr Asp Phe Pro Thr Pro Leu Val Thr Gln Asp His
                340                 345                 350

Ile Thr Ala Val Tyr Glu Leu Thr Ala Ala Val Gln Ala Val Leu Asp
        355                 360                 365

Ile Phe Ile Asn Tyr Asp Thr Lys Ser Leu Val Ala Ser Pro Ser Leu
        370                 375                 380

Val Tyr Ala Ala Arg Ala Ala Tyr Ala Leu Tyr Val Leu Ala Lys Leu
385                 390                 395                 400

Tyr Ile Ala Val Thr Ala Pro Gly Asn Thr Leu Gly Thr Ile Leu Asp
```

```
              405                 410                 415
Ala Ser Ile Leu Ala Leu Pro Glu Tyr Ala Asp Arg Leu Ala Thr Cys
                420                 425                 430

Gly Ser Arg Ile Arg Ala Leu Asp Glu Arg Cys Gly Pro Ala Arg Ile
            435                 440                 445

Met His Cys Ala Pro Ala Ile Lys Asp Trp Tyr Leu Asn Tyr Thr Gln
    450                 455                 460

Phe Leu Ser Ser Asn Ala Ala Leu Ala Gln Ser Ile Gln Val Ser Asn
465                 470                 475                 480

Asp Asn Val Ala Glu Ala Gln Met Thr Leu Pro Pro Leu Gln Asp Asn
                485                 490                 495

Thr Asn Ala Phe Ser Asn Ile Pro Pro Asp Trp Glu Asn Leu Leu Met
            500                 505                 510

Phe Gly Asp Ser Ser Thr Asp Tyr Gly Phe Asp Gln Leu Phe Ala Glu
        515                 520                 525

Pro Ile Pro Leu Gln Leu Glu Gln Pro Ile Phe Ala Asn Thr Ile Pro
    530                 535                 540

Thr Ala Phe Ala Thr Lys
545                 550

(2) INFORMATION FOR SEQ ID NO:10:

(i) SEQUENCE CHARACTERISTICS:
        (A) LENGTH: 924 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..921

(xi) SEQUENCE DESCRIPTION: SEQ ID NO:10:

ATG GCA ACT GAA CTC CCC ACC ACA AAC GGC CAC AGC GCA CAG GAT GGC      48
Met Ala Thr Glu Leu Pro Thr Thr Asn Gly His Ser Ala Gln Asp Gly
 1               5                  10                  15

GAG AAC AAC TTT GCC GTC AAG GCC GGT CTG GCA CGC ATG TTG AAG GGT      96
Glu Asn Asn Phe Ala Val Lys Ala Gly Leu Ala Arg Met Leu Lys Gly
                20                  25                  30

GGA GTC ATC ATG GAC GTT GTC AAC GCT GAG CAA GCG CGG ATA GCA GAA     144
Gly Val Ile Met Asp Val Val Asn Ala Glu Gln Ala Arg Ile Ala Glu
            35                  40                  45

GAA GCC GGT GCT TCA GCC GTC ATG GCC CTC GAG CGC GTG CCC GCA GAC     192
Glu Ala Gly Ala Ser Ala Val Met Ala Leu Glu Arg Val Pro Ala Asp
    50                  55                  60

ATT CGA TCC CAA GGT GGT GTC GCA CGT ATG AGC GAC CCC AAG ATG ATC     240
Ile Arg Ser Gln Gly Gly Val Ala Arg Met Ser Asp Pro Lys Met Ile
65                  70                  75                  80

AAG GAG ATC ATG GAC ACA GTC ACA ATC CCC GTC ATG GCC AAG GCG CGA     288
Lys Glu Ile Met Asp Thr Val Thr Ile Pro Val Met Ala Lys Ala Arg
                85                  90                  95

ATT GGA CAC TTT GTC GAA TGC CAG ATC CTC GAA GCC CTA GGC GTA GAC     336
Ile Gly His Phe Val Glu Cys Gln Ile Leu Glu Ala Leu Gly Val Asp
            100                 105                 110

TAC ATT GAC GAA TCC GAA GTC CTC ACC CCC GCC GAC GCT ATT CAC CAC     384
Tyr Ile Asp Glu Ser Glu Val Leu Thr Pro Ala Asp Ala Ile His His
    115                 120                 125

GTC TCC AAG CAC CCC TTC CGC ATT CCC TTC GTC TGC GGC TGC CGG GGC     432
```

```
Val Ser Lys His Pro Phe Arg Ile Pro Phe Val Cys Gly Cys Arg Gly
        130                 135                 140

CTC GGC GAA GCC CTT CGC CGC ATC TCG GAA GGT GCA GCC ATC ATC CGC      480
Leu Gly Glu Ala Leu Arg Arg Ile Ser Glu Gly Ala Ala Ile Ile Arg
145                 150                 155                 160

ACA AAG GGC GAA GCC GGA ACC GGC GAC GTC ATT GAG GCT GTC CGC CAC      528
Thr Lys Gly Glu Ala Gly Thr Gly Asp Val Ile Glu Ala Val Arg His
                165                 170                 175

ATG CGT ACC GTA AAC AGC GAG ATT GCC CGC GCA AAG AGC ATG TCA GAG      576
Met Arg Thr Val Asn Ser Glu Ile Ala Arg Ala Lys Ser Met Ser Glu
            180                 185                 190

GAG GAG CTC CGT GTC TAC GCA AAG GAG CTT CAG GTC GAC TAT GCG CTG      624
Glu Glu Leu Arg Val Tyr Ala Lys Glu Leu Gln Val Asp Tyr Ala Leu
        195                 200                 205

CTC AAG GAG ACG GCT AAG CTT GGT CGT CTG CCT GTT GTC AAC TTT GCG      672
Leu Lys Glu Thr Ala Lys Leu Gly Arg Leu Pro Val Val Asn Phe Ala
210                 215                 220

GCG GGT GGT GTC GCA ACA CCC GCT GAT GCT GCG TTG ATG ATG CAG TTG      720
Ala Gly Gly Val Ala Thr Pro Ala Asp Ala Ala Leu Met Met Gln Leu
225                 230                 235                 240

GGT TGC GAT GGT GTC TTT GTT GGT AGC GGT ATC TTC AAG TCT GGA GAC      768
Gly Cys Asp Gly Val Phe Val Gly Ser Gly Ile Phe Lys Ser Gly Asp
                245                 250                 255

GCA GCC AAG AGG GCC AAG GCC ATC GTA CAG GCT GTT ACT CAC TAC AAA      816
Ala Ala Lys Arg Ala Lys Ala Ile Val Gln Ala Val Thr His Tyr Lys
            260                 265                 270

GAC CCC AAG GTG CTC ATG GAA GTC AGC ATG GAT TTG GGT GAG GCC ATG      864
Asp Pro Lys Val Leu Met Glu Val Ser Met Asp Leu Gly Glu Ala Met
        275                 280                 285

GTT GGT ATC AAC TGC GGT ACA ATG GGC GAG GAG GAG AAG CTT GCT AAG      912
Val Gly Ile Asn Cys Gly Thr Met Gly Glu Glu Glu Lys Leu Ala Lys
290                 295                 300

AGG GGA TGG TAG                                                      924
Arg Gly Trp
305

(2) INFORMATION FOR SEQ ID NO:11:

(i) SEQUENCE CHARACTERISTICS:
        (A) LENGTH: 307 amino acids
        (B) TYPE: amino acid
        (D) TOPOLOGY: linear (ii) MOLECULE TYPE: protein (xi) SEQUENCE DESCRIPTION: SEQ ID NO:11:

Met Ala Thr Glu Leu Pro Thr Thr Asn Gly His Ser Ala Gln Asp Gly
1               5                   10                  15

Glu Asn Asn Phe Ala Val Lys Ala Gly Leu Ala Arg Met Leu Lys Gly
                20                  25                  30

Gly Val Ile Met Asp Val Val Asn Ala Glu Gln Ala Arg Ile Ala Glu
            35                  40                  45

Glu Ala Gly Ala Ser Ala Val Met Ala Leu Glu Arg Val Pro Ala Asp
        50                  55                  60

Ile Arg Ser Gln Gly Gly Val Ala Arg Met Ser Asp Pro Lys Met Ile
65                  70                  75                  80

Lys Glu Ile Met Asp Thr Val Thr Ile Pro Val Met Ala Lys Ala Arg
                85                  90                  95

Ile Gly His Phe Val Glu Cys Gln Ile Leu Glu Ala Leu Gly Val Asp
            100                 105                 110
```

-continued

```
Tyr Ile Asp Glu Ser Glu Val Leu Thr Pro Ala Asp Ala Ile His His
        115                 120                 125

Val Ser Lys His Pro Phe Arg Ile Pro Phe Val Cys Gly Cys Arg Gly
    130                 135                 140

Leu Gly Glu Ala Leu Arg Arg Ile Ser Glu Gly Ala Ala Ile Ile Arg
145                 150                 155                 160

Thr Lys Gly Glu Ala Gly Thr Gly Asp Val Ile Glu Ala Val Arg His
                165                 170                 175

Met Arg Thr Val Asn Ser Glu Ile Ala Arg Ala Lys Ser Met Ser Glu
            180                 185                 190

Glu Glu Leu Arg Val Tyr Ala Lys Glu Leu Gln Val Asp Tyr Ala Leu
        195                 200                 205

Leu Lys Glu Thr Ala Lys Leu Gly Arg Leu Pro Val Val Asn Phe Ala
    210                 215                 220

Ala Gly Gly Val Ala Thr Pro Ala Asp Ala Ala Leu Met Met Gln Leu
225                 230                 235                 240

Gly Cys Asp Gly Val Phe Val Gly Ser Gly Ile Phe Lys Ser Gly Asp
                245                 250                 255

Ala Ala Lys Arg Ala Lys Ala Ile Val Gln Ala Val Thr His Tyr Lys
            260                 265                 270

Asp Pro Lys Val Leu Met Glu Val Ser Met Asp Leu Gly Glu Ala Met
        275                 280                 285

Val Gly Ile Asn Cys Gly Thr Met Gly Glu Glu Glu Lys Leu Ala Lys
    290                 295                 300

Arg Gly Trp
305
```

ISOLATED GENES AND PROTEINS ENCODING RESISTANCE TO PHOTOSENSITIZERS

FEDERALLY SPONSORED RESEARCH OR DEVELOPMENT

This invention was made with government support under grant numbers MCB-9205578 and MCB-9631375 from the National Science Foundation, and NRI Competitive Grant number 9601197 from the USDA.

BACKGROUND OF THE INVENTION

Cercospora species are a highly successful group of fungal pathogens that cause disease on a diversity of host plants, including corn, sugar beet, tobacco, coffee, soybean, and banana, as well as many ornamental and weed species. For example, the Cercospora species *C. nicotiniae, C. arachidicola, C. zeae-maydis, C. kikuchii, C. oryzae* and *C. beticola* are pathogenic to tobacco, peanut, corn, soybean, rice and sugar beet, respectively. The Cercospora species are aerial pathogens. In general, spores produced by these fungi germinate on leaf surfaces and then enter the leaf (i.e. through stomata). Fungal mycelium then kills leaf cells and causes severe blighting of the leaf tissue by spreading through intercellular spaces in leaf tissues. See M. E. Daub, *American Chemical Society Symposium Series* No. 339, pp. 271–80 (J. R. Heitz and K. R. Downum, eds., Washington, D.C., 1987). In addition to damaging leaf tissue, Cercospora species may also damage other plant tissues, such as the seed coat in soybean. Cercospora species cause major economic problems due not only to their world-wide distribution and wide host range, but also because naturally-occurring resistance to the disease has not been identified in many host species.

One of the reasons for the success of this group of pathogens appears to be their production of cercosporin, a perylenequinone phytotoxin and a photosensitizer. Cercosporin is produced by many members of the genus Cercospora, and has near universal toxicity to plants. Cercosporin is also toxic to mice, bacteria, and many fungi. See R. B. Batcharova et al., *Phytopathology* 82, 642–46 (1992); C. Balis and M. G. Payne *Phytopathology* 61, 1477–84 (1971); M. E. Daub *Phytopathology* 77, 1515–20 (1987); A. O. Fajola, *Physiol. Plant. Pathol.* 13, 157–64 (1978); S. Yamazaki et al., *Agric. Biol. Chem.* 39, 287–88 (1975). Cercosporin has additionally been shown inactivate protein kinase C and to be cytotoxic to human tumor cells. See T. Tamaoki and H. Nakano *Bio/Technology* 8, 732–35 (1990). These observations suggest that cercosporin has almost universal toxicity to cells, and that resistance is due to active defense mechanisms present in the few resistant organisms. Production of cercosporin appears critical for successful pathogenesis, as fungal mutants deficient in cercosporin synthesis are unable to parasitize their host plants (R. G. Upchurch et al., *Appl. Envir. Biol.* 57, 2940–45 (1991)).

The presence of light has been shown to be critically important in the development of disease symptoms on hosts susceptible to Cercospora infection, and symptom development in infected plants is enhanced by high light intensities. See, e.g., M. E. Daub and M. Ehrenshaft, *Physiol. Plant* 89, 227–36 (1993); L. Calpouzos, *Ann. Rev. Phytopathol.* 4, 369–390 (1967). The role of cercosporin as a photosensitizer is thus related to its ability to cause toxicity and injury in cells. Although cercosporin was the first toxin synthesized by plant pathogens to be recognized as a photosensitizer, numerous other plant pathogenic fungi also produce perylenequinone toxins and other compounds that are photosensitizers. The production of photoactivated perylenequinones by such a diversity of plant pathogens suggests that photosensitization may be a more common plant pathogenesis factor than has been previously recognized.

Virtually the only organisms which show resistance to cercosporin are the Cercospora fungi themselves, and some related fungi that produce similar toxins. Attempts to obtain resistant plants and fungi through mutagenesis and selection of cells in culture have not been successful. M. Ehrenshaft et al., (*Phytopathology* 86, S11 (Abstract 93A) (Supplement 1996)) report using a wild type *C. nicotianae* genomic library to isolate cosmid clones that complement two classes of *C. nicotianae* mutants which are sensitive to cercosporin. Transformation of the mutants with one of the clones restored wild type resistance to cercosporin and other photosensitizers. However, isolation and sequencing of the specific genes responsible for the resistance to the photosensitizers is not described therein.

It would thus be highly desirable to isolate genes which encode resistance to photosensitizers such as cercosporin. Moreover, it would be desirable to provide plants and other organisms resistant to diseases caused by Cercospora species and other pathogenic fungi that produce photosensitizers.

SUMMARY OF THE INVENTION

A first aspect of the present invention is an isolated nucleic acid molecule that, upon expression, provides or increases resistance to a photosensitizer in a cell.

A further aspect of the present invention is an isolated nucleic acid molecule that, upon expression, provides or increases resistance to cercosporin in a cell.

A further aspect of the invention is a transformed cell comprising a chimeric gene, the gene comprising a nucleic acid molecule of the present invention operably linked with a promoter.

A further aspect of the invention is a method for increasing resistance to a photosensitizer in cell, comprising transforming the cell with a nucleic acid molecule of the present invention.

A further aspect of the invention is a method of increasing resistance in a cell to a pathogen, comprising transforming the cell with a nucleic acid of the present invention.

A further aspect of the invention is a method of increasing resistance in a cell to singlet oxygen comprising transforming the cell with a nucleic acid of the present invention.

A further aspect of the invention is an expression cassette comprising a chimeric gene, the gene comprising a nucleic acid molecule of the present invention operably linked with a promoter.

A further aspect of the invention is a transformed plant, comprising either an expression cassette of the present invention, or a chimeric gene as described above.

An further aspect of the present invention is a method for increasing resistance to a photosensitizer in plant, comprising transforming the plant with an expression cassette of the present invention.

A further aspect of the invention is a method of increasing resistance in a plant to infection by a fungal pathogen, comprising transforming the plant with an expression cassette of the present invention.

A further aspect of the invention is a method of selecting transformed fungal or plant cells, using a transformation construct that includes a nucleic acid molecule of the present invention.

BRIEF DESCRIPTION OF THE DRAWINGS

FIG. 1 sets forth the nucleotide sequence of the *Cercospora nicotianae* gene sor1 that encodes resistance to cercosporin (SEQ ID NO:1).

FIG. 2 sets forth the amino acid sequence of a polypeptide that provides resistance to cercosporin and which is encoded by the *Cercospora nicotianae* gene sor1 (SEQ ID NO:2).

FIG. 3A sets forth the partial nucleotide sequence of the homologue to the *C. nicotianae* sor1 gene isolated from *Alternaria alternata* (SEQ ID NO:3).

FIG. 3B sets forth the predicted partial amino acid sequence (SEQ ID NO:4) of the protein encoded by the *Alternaria alternata* nucleic acid sequence set forth in FIG. 3A. The predicted amino acid sequence represents the C-terminus of the protein encoded by the *A. alternata* gene.

FIG. 4A sets forth the alignment between the partial nucleotide sequence of the *A. alternata* gene (SEQ ID NO:3) and a fragment of the *C. nicotianae* sor1 gene (SEQ ID NO:5). "AAIT7" indicates the *A. alternata* gene sequence, while "CSG" indicates the *C. nicotianae* sor1 gene fragment sequence. The "=" sign between the two sequences indicates that the aligned residues are identical.

FIG. 4B sets forth the alignment between the predicted C-terminus amino acid sequence of the *A. alternata* gene (SEQ ID NO:6) and a fragment of the *C. nicotianae* sor1 gene (SEQ ID NO:7). "AAHOMOLOG" represents the amino acid sequence of a portion of the *A. alternata* gene; "MAYBE2" represents the amino acid sequence of a fragment of the *C. nicotianae* sor1 gene. The "=" sign indicates that aligned residues are identical, while the "–" sign indicates that the aligned residues are similar. "Similar" residues are as follows: A, S, and T are deemed similar to each other; D and E are similar; N and Q are similar; R and K are similar; I, L, M and V are similar; and F, Y and W are similar.

FIG. 4C sets forth the alignment between the predicted amino acid sequence of the *A. alternata* gene product (SEQ ID NO:11) and the *C. nicotianae* sor1 gene product (SEQ ID NO:2). The "=" sign indicates that aligned residues are identical, while the "–" sign indicates that the aligned residues are similar. "Similar" residues are as described above.

DETAILED DESCRIPTION OF THE INVENTION

The present invention now will be described more fully hereinafter with reference to the accompanying Figures, in which certain embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Nucleotide sequences are presented herein by single strand only, in the 5' to 3' direction, from left to right. Amino acid sequences disclosed herein are presented in the amino to carboxy direction, from left to right, unless otherwise indicated. The amino and carboxy groups are not presented in the sequence. Nucleotides and amino acids are represented herein in the manner recommended by the IUPAC-IUB Biochemical Nomenclature Commission.

As used herein, the terms "protein" and "polypeptide" are used interchangeably, and refer to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

As used herein, the term "photosensitizer" refers to a light-activated compound, which, in the presence of light, reacts with oxygen to produce compounds (e.g., active oxygen species) that are damaging and toxic to cells. Photosensitizers are a group of structurally diverse compounds that have in common the ability to sensitize cells to light. More specifically, photosensitizers absorb light energy and are converted to an active state, which active state reacts with oxygen, either by radical reactions through a reducing substrate (type I reaction) or directly by an energy transfer mechanism (type II reaction). J. D. Spikes, *The Science of Photobiology* 2d. Edition, pp. 79–110 (K. C. Smith, ed., Plenum Press, New York 1989). Type I reactions lead to the production of a variety of reactive species, including a diversity of radical oxygen species such as superoxide ($O_2^-$), hydrogen peroxide ($H_2O_2$), and the hydroxy radical ($OH^-$). The Type II reaction leads to the production of one of the most reactive and toxic of the oxygen species, the active singlet state of oxygen (singlet oxygen or $^1O_2$). Exposure of cells to photosensitizers and light may lead to the destruction of critical cellular components such as lipids, proteins and DNA, and often leads to cell death. Within the scope of the present invention, it is specifically intended that the term "photosensitizer" include compounds that react with oxygen through both Type I and Type II pathways, and include compounds that, upon exposure to light and reaction with oxygen, produce both radical forms of oxygen and the active singlet form of oxygen.

Photosensitizer compounds as defined by the present invention may or may not be produced by pathogenic fungi. Singlet oxygen-generating photosensitizers that are produced by pathogenic fungi are, in general, perylenequinone toxins, and include, but are not limited to, cercosporin (produced by Cercospora spp., e.g., *C. nicotianae, C. kikuchii, C. oryzae*); the elsinochromes (e.g., elsinochrome A, produced by species of Elsinoe and Sphaceloma); phleichrome (isolated from cucumbers infected with *Cladosporium cucumerinum* and from *Cl. phlei* and *Cl. herbarum*); the shiraiachromes (isolated from the bamboo pathogen *Shiraia bambusicola*); the hypocrellins (isolated from, e.g., the bamboo pathogen *Hypocrella bambusae*); alteichin, altertoxins I, II, and III, and alterlosin I and II (isolated from Altertiaria spp.); stemphyltoxin III (isolated from Alternaria spp. and *Stemphylium botryosum* and the perylenequinone toxins produced by the Scolecotrichum genera. See, e.g., J. C. Overseem and A. K. Sijpesteijn, *Phytochemistry* 6, 99–105 (1967); D. J. Robeson and M. A. F. Jalal, *Biosci. Biotech. Biochem.* 56 949–52 (1992); H. Wu et al., *J. Nat. Products* 5, 948–51 (1989); V. M. Davis and M. E. Stack, *Appl. Environ. Microbiol.* 55, 7–14 (1991). Other photosensitizers, as defined in the present invention include the compounds rose bengal, hematoporphyrin, eosin Y, methylene blue and toluidine blue.

The present invention is drawn to compositions and methods for providing or increasing cellular resistance to photosensitizers in organisms that are sensitive to photosensitizers. The compositions are proteins and the genes encoding them, which act to provide or increase cellular resistance to photosensitizers in such organisms. The proteins and the genes encoding resistance to photosensitizers, and the methods described herein that utilize these compounds, are useful in providing cellular resistance to pathogens that produce photosensitizers, and survival of these cells, particularly after pathogen attack. These same compositions and methods also provide or increase resistance to singlet oxygen itself.

One aspect of the invention is drawn to proteins which are involved in providing resistance in a cell or an organism to a photosensitizer. The photosensitizer resistance proteins of the invention encompass a novel class of fungal proteins. The amino acid sequence of the photosensitizer resistance protein isolated from *C. nicotianae* is set forth in FIG. 2 and is also provided herein as SEQ ID NO:2. However, the proteins are conserved in fungi and in other organisms. Thus, as discussed below, methods are available for the identification and isolation of genes and proteins from any organism. Likewise, sequence similarities can be used to identify and isolate other genes and proteins that encode resistance to photosensitizers. The proteins function to inhibit the spread of infection caused by pathogenic fungi that encode photosensitizers, and control resistance to such compounds in a number of organisms, including plants, bacteria, insects and animals. Therefore, the proteins are useful in a variety of settings involving the control of disease and toxicity resistance in plants and other organisms.

Modifications of such proteins are also encompassed by the present invention. Such modifications include substitution of amino acid residues, deletions, additions, and the like. Accordingly, the proteins of the invention include naturally occurring fungal proteins and modifications thereof.

The nucleolide sequences encoding the novel proteins are also provided. The gene sor1 from *C. nicotianae* is set forth in FIG. 1 and provided herein as SEQ ID NO:1. This gene encodes the novel *C. nicotianace* protein, which confers resistance to several photosensitizers, including cercosporin. The *C. nicotianae* gene sor1 can be utilized to isolate homologous genes from other organisms. For example, FIG. 2 provides the nucleotide sequence of an *Alternaria alternata* gene with significant sequence homology to *C. nicotianae* sor1 which *A. alternata* gene was isolated using the sor1 gene.

Nucleic acids and proteins of the present invention find use in preventing or increasing resistance in cells and organisms to photosensitizers. The proteins are also particularly useful in protecting organisms against pathogenic infection. In this manner, the organism is transformed with a nucleotide sequence encoding the protein. According to the present invention, organisms transformed in this manner may be plants, bacteria, fungi, and animals, with plants being preferred. The expression of the protein in the organism prevents toxicity and injury caused by photosensitizers, and confers or increases resistance to infection by fungal pathogens.

Although the compounds and methods of the present invention are useful in providing resistance to infection by any fungal pathogen that produces a photosensitizer, the present invention finds particular use in providing protection against infection caused by (and photosensitizers produced by) the over 2,000 fungal pathogens of the Cercospora species. This group of fungal pathogens includes, but is not limited to: *C. arachidicola* (infecting peanuts), *C. ariminiensis, C. asparagi* (infecting asparagus), *C. bertoreae, C. beticola* (infecting sugar beets), *C. bizzozeriana, C. brassicicola* (infecting Brassica, e.g., cabbage, rape), *C. canescens* (infecting e.g., soybean, tomato), *C. carotae* (infecting carrots), *C. chenopodii, C. cistineareum, C. cladosporioides, C. diazu, C. erysimi, C. hayli, C. kikuchii* (infecting soybean), *C. longpipes* (infecting sugarcane), *C. malvicola, C. medicaginus* (infecting trifolium), *C. nicotianae* (infecting tobacco), *C. oryzae* (infecting rice), *C. personata, C. planitaginis, C. ricinella, C. setariae, C. unamunoi, C. violae,* and *C. zeamaydis* (infecting corn).

Methods are readily available in the art for the hybridization of nucleic acid sequences. Sequences that code for photosensitizers from a broad range of species may be isolated according to well known techniques based on their sequence homology to the coding sequences (e.g., sor1) set forth herein. In these techniques, all or part of the known coding sequence is used as a probe which selectively hybridizes to other photosensitizer resistance coding sequences present in a population of cloned genomic DNA fragments or cDNA fragments (i.e. genomic or cDNA libraries) from a chosen organism.

For example, the entire sequence provided as SEQ ID NO:1, or portions thereof may be used as probes capable of specifically hybridizing to corresponding coding sequences and messenger RNAs. To achieve specific hybridization under a variety of conditions, such probes include sequences that are unique among coding sequences that encode resistance to photosensitizers (hereinafter resistance coding sequences), and are preferably at least about 10 nucleotides in length, and most preferably at least about 20 nucleotides in length. Such probes may be used to amplify resistance coding sequences from a chosen organism by the well-know process of polymerase chain reaction (PCR). This technique may be used to isolate additional resistance coding sequences from a desired organism or as a diagnostic assay to determine the presence of resistance coding sequences in an organism.

Such techniques include hybridization screening of plated DNA libraries (either plaques or colonies; see, e.g., Sambrook et al., *Molecular Cloning*, eds., Cold Spring Harbor Laboratory Press (1989)) and amplification by PCR using oligonucleotide primers corresponding to sequence domains conserved among the amino acid sequences (see, e.g. Innis et al., *PCR Protocols, a Guide to Methods and Applications*, eds., Academic Press (1990)).

For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively), to DNA encoding resistance to photosensitizers disclosed herein in a standard hybridization assay. See J. Sambrook et al., *Molecular Cloning, A Laboratory Manual 2d Ed.* (1989) Cold Spring Harbor Laboratory. In general, sequences which code for a photosensitizer resistance protein and hybridize to the *C. nicotianae* gene disclosed herein as SEQ ID NO:1 will be at least 50% homologous, 70% homologous, and even 85% homologous or more with the *C. nicotianae* sequence. That is, the sequence similarity of sequences may range, sharing at least about 50%, about 70%, and even about 85%, 90%, 95% or more sequence similarity.

Also provided are mutant forms of the *C. nicotianae* photosensitizer resistance gene, and the proteins they encode. Methods for mutagenesis and nucleotide sequence alterations are well known in the art. See, for example, Kunkel, T. (1985) *Pro. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, NY (1983) and the references cited therein. Thus, the genes and nucleotide sequences of the invention include both the naturally occurring sequences as well as mutant forms. Likewise, the proteins of the invention encompass both naturally occurring proteins as well as variations and modified forms thereof.

The nucleotide sequences encoding the proteins or polypeptides of the invention are useful in the genetic manipulation of organisms, including bacteria, fungi, plants and animals. This aspect of the invention is illustrated herein with respect to the genetic manipulation of plants. In this manner, the nucleotide sequences of the present invention are provided in expression cassettes for expression in the plant of Interest. The cassette will include 5' and 3' regulatory sequences operably linked to the gene of interest. The term "operably linked," as used herein, refers to DNA sequences on a single DNA molecule which are associated so that the function of one is affected by the other. Thus, a promoter is operatively associated with a gene of the present invention when it is capable of affecting the expression of the gene of the present invention (i.e., the gene is under the transcriptional control of the promoter). The promoter is said to be "upstream" from the gene, which is in turn said to be "downstream" from the promoter.

Expression cassettes of the present invention include, 5'–3' in the direction of transcription, a promoter as discussed above, a gene of the present invention operatively associated with the promoter, and, optionally, a termination sequence including stop signal for RNA polymerase and a polyadenylation signal for polyadenylase (e.g., the nos terminator). All of these regulatory regions should be capable of operating in the cells of the tissue to be transformed. The 3' termination region may be derived from the same gene as the transcriptional initiation region or may be derived from a different gene.

The cassette may additionally contain at least one additional gene to be cotransformed into the organism. Alternatively, the gene(s) of interest can be provided on another expression cassette. Where appropriate, the gene(s) may be optimized for increased expression in the transformed plant.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA*, 86:6126–6130); potyvirus leaders, for example, TEV leader (Tobacco Etch Virus) (Allison et al. (1986); MDMV leader (Maize Dwarf Mosaic Virus); *Virology*, 154:9–20), and human immunoglobulin heavy-chain binding protein (BiP), (Macejak, D. G., and P. Sarnow (1991) *Nature*, 353:90–94; untranslated leader from the coat protein mRNA of alfalfa mosaic virus (AMV RNA 4), (Jobling, S. A., and Gehrke, L., (1987) *Nature*, 325:622–625; tobacco mosaic virus leader (TMV), (Gallie, D. R. et al. (1989) *Molecular Biology of RNA*, pages 237–256; and maize chlorotic mottle virus leader (MCMV) (Lommel. S. A. et al. (1991) *Virology*, 81:382–385). See also, Della-Cioppa et al. (1987) *Plant Physiology*, 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions and methods of the present invention can be used to transform any plant, or any portion of a plant thereof. In this manner, genetically modified plants, plant cells, plant tissue (e.g., plant leaves, stems, roots), seeds, seed coats, and the like can be obtained. Transformation protocols may vary depending on the type of plant or plant cell, i.e. monocot or dicot, targeted for transformation. Suitable methods of transforming plant cells include microinjection (Crossway et al. (1986) Biotechniques 4:320–334), electroporation (Riggs et al. (1986) *Proc. Natl. Acad. Scl. USA*, 83:5602–5606, Agrobacterium mediated transformation (Hinchee et al. (1988) *Biotechnology*, 6:915–921), direct gene transfer (Paszkowski et al. (1984) *EMBO J.*, 3:2717–2722), and ballistic particle acceleration (see, for example, Sanford et al., U.S. Pat. No. 4,945,050; WO91/10725 and McCabe et al. (1988) *Biotechnology*, 6:923–926). Also see, Weissinger et al. (1988) *Annual Rev. Genet.*, 22:421–477; Sanford et al. (1987) *Particulate Science and Technology*, 5:27–37 (onion); Christou et al. (1988) *Plant Physiol.* 87:671–674(soybean); McCabe et al. (1988) *Bio/Technology*, 6:923–926 (soybean); Datta et al. (1990) *Biotechnology*, 8:736–740(rice); Klein et al. (1988) *Proc. Natl. Acad. Sci. USA*, 85:4305–4309(maize); Klein et al. (1988) *Biotechnology*, 6:559–563 (maize); WO91/10725 (maize); Klein et al. (1988) *Plant Physiol.*, 91:440–444 (maize); Fromm et al. (1990) *Biotechnology*, 8:833–839; and Gordon-Kamm et al. (1990) *Plant Cell*, 2:603–618 (maize); Hooydaas-Van Slogteren & Hooykaas (1984) *Nature* (London), 311:763–764; Bytebier et al. (1987) *Proc. Natl. Acad. Sci. USA*, 84:5345–5349 (Lihaceae); De Wet et al. (1985) In *The Experimental Manipulation of Ovule Tissues*, ed. G. P. Chapman et al., pp. 197–209. Longman, N.Y. (pollen); Kaeppler et al. (1990) *Plant Cell Reports*, 9:415–418; and Kaeppler et al. (1992) *Theor. Appl. Genet.*, 84:560–566 (whisker-mediated transformation); D Halluin et al. (1992) *Plant Cell*, 4:1495–1505 (electroporation); Li et al. (1993) *Plant Cell Reports*, 12:250–255 and Christou and Ford (1995) *Annals of Botany*, 75:407–413 (rice); Osjoda et al. (1996) *Nature Biotechinology*, 14:745–750 (maize via *Agrobacterium tumejaciens*); all of which are herein incorporated by reference.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical merist, ms, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species).

Plants which may be employed in practicing the present invention include (but are not limited to) tobacco (*Nicotiana tabacum*), potato (*Solanum tuberosum*), soybean (*glycine max*), peanuts (*Arachis hypogaea*), Brassica species (e.g., rape, canola), sorghum (*Sorghum bicolor*), cotton (*Gossypium hirsutum*), sweet potato (*Ipomoea batatus*), cassava (*Maninot esclenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), Cashew (*Anacardium occidentale*), macadamia (*Macadamia integrifolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), carrots, asparagus, lettuce (e.g., *Lactuea sativa*), green beans (*Phaseolus vulgaris*), lima beans (*Phaseolus limensis*), peas (Lathyrus spp.) and members of the genus Cucumis such as cucumber (*C. sativus*), cantaloupe (*C. cantalupensis*), and musk melon (*C. melon*). Ornamentals include azalea (Rhododendron spp.), hydrangea (*Macrophylia hydrangea*), hibiscus (*Hibiscus rosasanensis*), roses (Rosa spp.), tulips (Tulipa spp.), daffodils (Narcissus spp.), petnunias (*Petunia hybrida*), carnation (*dianthius caryopliyllus*), poinsettia (*Euphorbia pulcherima*), and chyrsanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga nmenziesii*); Western hemlock (*Tsuga canadlensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The cells which have been transformed may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

When a gene encoding resistance to a photosensitizers is included in an expression cassette, the gene may be used in combination with a marker gene, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complementation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase, providing indigo production, luciferase, providing visible light production, NPTII, providing kanamycin resistance or G418 resistance, HPT, providing hygromycin resistance, and the mutated aroA gene, providing glyphosate resistance. Selectable marker genes and reporter genes are known in the art. See generally, G. T. Yarranton (1992) *Curr. Opin. Biotech.*, 3:506–511; Christopherson et al. (1992) *Pro. Natl. Acad. Sci. USA*, 89:6314–6318; Yao et al. (1992) *Cell*, 71:63–72; W. S. Reznikoff (1992) *Mol. Microbiol.*, 6:2419–2422; Barkley et al. (1980) *The Operon*, pp. 177–220; Hu et al. (1987) *Cell*, 48:555–566; Brown et al. (1987) *Cell*, 49:603–612; Figge et al. (1988) *Cell*, 52:713–722; and, Deuschle et al. (1989) *Proc. Natl. Acad. Aci. USA*, 86:5400–5404. Other genes of interest may additionally be included. The respective genes may be contained in a single expression cassette, or alternatively in separate cassettes. Methods for construction of the cassettes and transformation methods have been described above.

As discussed, the genes of the invention can be manipulated to enhance disease resistance in plants. In this manner, the expression or activity of the gene encoding resistance to photosensitizers is altered. Such means for alteration of the gene include co-suppression, antisense, mutagenesis, alteration of the sub-cellular localization of the protein, etc. In some instances, it may be beneficial to express the gene from an inducible promoter, particularly from a pathogen inducible promoter. Such promoters include those from pathogenesis-related proteins (PR proteins) which are induced following infection by a pathogen; e.g., PR proteins, SAR proteins, beta-1,3-glucanase, chitinase, etc. See, for example, Redolfi et al. (1983) *Neth. J. Platut Pathol.* 89:245–254; Uknes et al.

Nucleotide sequences of the present invention are also useful as selectable markers in transforming plant or fungal cells. A pyridoxine-deficient *Aspergillus flavus* transformed with SOR1 was found to be able to grow on minimal media lacking pyridoxine. Accordingly, the SOR1 gene may be used as a marker gene in combination with a second gene, where it is desired to transform plants with the second gene. Successful transformation is indicated by the ability of the transformant to grow on media lacking pyridoxine, where the original (untransformed) plant is unable to grow. Methods and constructs for selectable marker use are well-known in the art.

Using the present nucleotide sequences in methods of selecting, from a plurality of cells that have undergone a transformation procedure, only those cells that have been successfully transformed, would comprise transforming cells from an organism that is unable to grow (or grows poorly) in the absence of exogenous pyridoxine (for example, in medium that does not contain pyridoxine). Numerous suitable transformation procedures are known in the art; the selection of a suitable procedure would depend on the cells being transformed and the desired effect. Selection of suitable transformation procedures will be apparent to those skilled in the art. The cells are subjected to a transformation procedure using a construct comprising a heterologous DNA sequence of interest and a second DNA sequence according to the present invention, such as SEQ ID NO:1 or the open reading frame thereof. The cells are then placed on medium lacking pyridoxine; only those cells that are able to grow on the medium have been successfully transformed.

The present invention is more fully illustrated by the following Examples, which are set forth to illustrate the present invention and are not to be construed as limiting thereof.

EXAMPLE 1

Isolation of Cercosporin-Sensitive Mutants

Mutants of *Cercospora nicotianae* which are sensitive to cercosporin are isolated according to procedures described in A. E. Jenns et al., *Photochem. Photobiol.* 61, 488–493 (1995) and A. E. Jenns and M. E. Daub, *Phytopathol.* 85, 96–912 (1995). The mutants are isolated from UV-mutagenized mycelial protoplasts, and screened for cercosporin sensitivity by replica-plating colonies on cercosporin-containing medium. All isolation and screening is done under conditions that suppress e ndogenous cercosporin synthesis (A. E. Jenns et al., *Phytopathol.* 79, 213–219 (1989). Six cercosporin-senisitive (CS) mutants are isolated, and are characterized into two phenotypic classes. Five of the mutants (CS2, CS6, CS7, CS8, and CS9, designated class 1) are totally inhibited when grown on medium containing cercosporin at concentrations as low as 1 $\mu$M. The sixth mutant (CS10, designated class 2), is partially inhibited by 10 $\mu$M cercosporin, but not at lower concentrations. When the mutants are assayed by fluorescence microscopy, the class 1 mutants are found to be incapable of reducing cercosporin. The partially-sensitive CS10, however, is normal in cercosporin-reducing ability.

Further phenotypic characterization is done according to the method of Jenns and Daub, supra. All of the mutants are capable of synthesizing cercosporin when grown Linder conditions that induce cercosporin synthesis. The class 1 mutants stop growing when cercosporin is produced, but, surprisingly, endogenous cercosporin production appears to have little effect on growth of CS10. Cercosporin sensitivity is not due to a general sensitivity of any of the mutants to light. As with other sensitive fungi, the mutants are able to be protected against cercosporin toxicity by the addition of reducing agents such as ascorbate, cysteine, and reduced glutathione. However, none of the mutants is altered in production of these compounds or in levels of total soluble or protein thiols, indicating that resistance is not due to endogenous production of these agents.

The mutants are also tested for resistance to five other singlet oxygen-generating photosensitizers: methylene blue, toluidine blue, rose bengal, eosin Y, and hematoporphyrin. Wild type *C. nicotianae* is highly resistant to all these photosensitizers, with the exception of rose bengal, which shows some toxicity to these fungi. Surprisingly, the class 1 sensitive mutants were completely inhibited by all of the photosensitizers. This level of sensitivity was unexpected, as even the most cercosporin-sensitive, naturally-occurring fungal species are capable of at least some growth on these compounds. Thus the class 1 mutants appear to be mutant in a gene which mediates resistance to a range of singlet oxygen-generating photosensitizers, and such a mutation results in levels of photosensitizer sensitivity not occurring in fungi in nature. In contrast, the sensitivity of mutant CS10 was specific to cercosporin; response of CS10 to the other photosensitizers was identical to that of wild type.

EXAMPLE 2

Isolation of Genes Encoding Resistance to Cercosporin

A genomic library is constructed from the *C. nicotianae* wild type strain (ATCC#18366) in a bialaphos-resistance-conferring plasmid, pBAR3 (Straubinger et al., *Fungal Genetics Newsletter* 39, 82–83 (1992), which is modified by addition of a COS site to allow the cloning of inserts of approximately 45 kb. Approximately 4,000 cosmid clones are isolated and stored individually in wells of microtitre plates. Estimating the size of the *C. nicotianae* haploid genome as equal to that of *N. crassa* ($4 \times 10^7$), the library is estimated to have a 99% probability of representing the entire genome as intact fragments.

DNA for transformation is prepared by growing each cosmid clone separately as 5 ml cultures and then pooling all cultures from one microtitre plate. Pooled DNA is then transformed into both CS10 and CS8. CS10 was chosen as it is the only mutant characterized by being partially cercosporin sensitive, unaffected in cercosporin reduction, and unaffected by other photosensitizers. CS8 is representative of the five class 1 mutants which are totally sensitive to both cercosporin and other photosensitizers and are unable to reduce cercosporin. CS8 was chosen since it grows well in the absence of cercosporin, sporulates well, and is the most easily transformed of the class 1 mutants. Transformants are selected for resistance to bialaphos, and then 300–400 transformants resulting from transformation with each plate of DNA are screened for resistance to cercosporin by growing them on medium containing 10 $\mu$M cercosporin.

Clones complementing both mutations are identified. Four colonies showing wild-type levels of resistance are recovered from the partially cercosporin-sensitive CS10transformed with DNA from one selected plate. Transformation of CS10 with DNA from individual clones of this plate resulted in the identification of a specific complementing cosmid clone, designated 30H2. Forty-two percent of CS10 colonies transformed with clone 30H2 exhibit a cercosporin resistance phenotype indistinguishable from that of the wild type.

Eleven CS8 colonies resulting from transformation with DNA from another selected exhibit wild-type levels of cercosporin resistance. A specific complementing cosmid clone, designated 18E1, is identified. Seventy-eight percent of CS8 colonies transformed with clone 18E1 show wild type levels of cercosporin resistance. Clone 18E1 also restores wild-type levels of resistance in CS8 to the five other singlet oxygen-generating photosensitizers, toluidine blue, methylene blue, eosin Y, hematoporphyrin and rose bengal.

As all the class 1 mutants (CS2, CS6, CS7, CS8, and CS9) share an identical phenotype. The phenotype of the class 1 mutants suggests that the resistance gene complementing them imparts resistance to $^1O_2$ specifically. Because of the differences in phenotype between CS10 and the class 1 mutants, it is thought that the mutations are hi different loci. This hypothesis is supported by transformation experiments;. Transformation of CS8 with clone 30H2 failed to restore any level of resistance to cercosporin. Similarly, clone 18E1 did not complement CS10.

EXAMPLE 3

Sequence Analysis of Genes Encoding Resistance to Cercosporin

Since the cosmids which complement CS8 and CS10 each contain more than 40 kb of *C. nicotanae* DNA, overlapping restriction fragments were subcloned to identify shorter sequences of DNA (5–10 kb) which confer cercosporin resistance. Complementing subclones from each cosmid were mapped, and a common restriction fragment used as a probe in northern analysis to determine that they hybridize to a single message. These probes were then used to identify full length cDNAs corresponding to the genes from 18E1 and 30H2 which confer resistance to photosensitizers.

Both the genomic fragments and the cDNAs are sequenced. The technique of primer-walking is used to generate nested deletions for sequencing, using an approach used previously to sequence the *C. nicotianae* phytoene dehydrogenase gene (M. Ehrenshaft and M. E. Daub, *Appl. Environ. Microbiol.* 60, 2766–2771 (1994)). Deletion clones are sequenced at the University of Georgia Molecular Genetics Facility (Athens, Ga., USA).

A gene located within clone 18E1 that confers cercosporin resistance (the gene is named sor1) to *C. nicotianae* was sequenced. The sequence analysis of sor1 revealed an open reading frame encoding a protein of 343 amino acid residues. The nucleotide sequence of the gene, in the 5' to 3' direction is given herein as SEQ ID NO:1 (see FIG. 1). The open reading frame of SEQ ID NO:1 is nucleotides 825–1853, inclusive.

The predicted amino acid sequence of the protein expressed by the isolated sor1 gene encoding cercosporin resistance is (in the NH$_2$-terminal to COOH-terminal) direction:

*Plant. Microb. Interact.* 8, 569–575 (1995)). Wild type *C. nicotianae* strain ATCC #18366 was transformed with a disrupted version of the SOR1 resistance genes. Southern analysis identified both transformants in which the disrupted gene replaced the wild-type copy, and transformants which contained both a wild-type and a disrupted version. Transformants were screened for loss or decrease in cercosporin resistance, and loss or decrease in resistance to the other singlet-oxygen-generating photosensitizers described above in Jenns et al. (1995), supra, and Ehrenshaft et al., (1995), supra.

The null mutants created by the above methods were completely sensitive to cercosporin and to other photosensitizers. These results confirm that SOR1 functions to provide resistance to cercosporin and other singlet-oxygen-generating photosensitizers.

The same methods as described above are used to confirm the function of the CRG1 gene.

EXAMPLE 5

Expression of Resistance Genes in *Aspergillus flavus*

The phenotype of the class 1 mutants suggests that the resistance gene complementing imparts resistance to singlet oxygen. If so, this gene (with or without the CS10complementing gene) may be useful in genetic engineering of other organisms for photosensitizer or singlet oxygen resistance.

| MASNGTSVSP | FRSQKNAAMA | VNDTPANGHA | EPSTITAASK | TN | KITSQN | DPQSSFAVKV | GLAQMLKGGV |
|---|---|---|---|---|---|---|---|
| IMDVVNAEQA | RIAEEAGACA | VMALERVPAD | IRKDGGVARM | SD | MIKDIM | NAVTIPVMAK | SRIGHFVECQ |
| ILQAIGVDYI | DESEVLTPAD | PVNHIDKSVY | NVPFVCGCKN | LG | RRISE | GAAMIRTKGE | AGTGDVVEAV |
| RHMQTVNAEI | AKASSASDAD | LRMMARELQC | DYNLLKQTAQ | LK | VVNFA | AGGIATPADA | ALMMQMGCDG |
| VFVGSGIFKS | GDAAKRAKAI | VQATTHYNDP | KVLAEVSSGL | GE | GINCD | KLPETQKLAT | RGW |
| (SEQ ID NO: 2) | | | | | | | |

EXAMPLE 3A

A gene located within clone 30H2 that also confers cercosporin resistance (the gene is named crg1) to *C. nicotianae* was sequenced; the nucleotide sequence of the gene, in the 5' to 3' direction is provided herein as SEQ ID NO:9. The sequence analysis of crg1 revealed an open reading frame (nucleotides 742–2391, inclusive, of SEQ ID NO:9) encoding a protein of 550 amino acid residues. The predicted amino acid sequence of the protein expressed by the isolated crg1 gene encoding cercosporin resistance is (in the NH$_2$-terminal to COOH-terminal direction) provided in SEQ ID NO:10.

EXAMPLE 4

Confirmation of Identity of Gene Encoding Resistance to Cercosporin

Mutant Cercospora that lacked the SOR1 gene (null mutants) have been produced. These mutants are sensitive to cercosporin and to other photosensitizers, as were the original mutants, thus confirming the function of SOR1.

After identification of the specific cercosporin resistance genes via mapping and sequencing of cDNA and genomic clones, complementing genes were used in gene disruption experiments in order to definitively confirm their identity. This approach was previously used to create carotenoid-minus mutants in *C. nicotianae* (Ehrenshaft et al., *Molec.*

The ability of the CS8 and CS10 complementing genes (individually and together) to impart resistance in heterologous organisms is tested using cercosporin-sensitive fungus *A. flavus*.

The cercosporin-resistance gene of the present invention is thus expressed in *A. flavus*. This fungus is used to test expression of the gene of the present invention because it is highly sensitive to cercosporin. M. E. Daub et al., *Proc. Natl. Acad. Sci USA* 89, 9588–9592 (1992). The *A. flavus* strain 656-2, generously provided by Dr. Gary Payne (Department of Plant Pathology, North Carolina State University, Raleigh, N.C.) is transformed with the gene according to the method of C. P. Woloshuk et al., *Appl. Environ. Microbiol.* 55, 86–90 (1989). Briefly, protoplasts are isolated from the *A. flavus* strain 656-2, a uridine-requiring mutant, by incubating myceliuni with an enzyme solution (10 mM NaPO$_4$, pH 5.8, 20 mM CaCl$_2$, 105 u/mL β-glucorinidase, Novozym 234, 1.2 M NaCl). The cercosporin-resistance gene sor1 is cloned into the plasmid pUC19pyr4. The plasmid contains the *Neurospora crassa* gene pyr4, which restores the ability to grow without uridine. Protoplasts are mixed with plasmid DNA, plated onto a regenerating medium (MPS) lacking uridine. Transformants that grow on these plates zare then inoculated onto potato dextrose agar containing μM cercosporin and inoculated in the light, and colony diameter measured at three days.

Alternatively, the sor1 open reading frame is cloned into the plasmid pBargpe1 downstream from the promoter of the Aspergillus gpdA gene. The promoter expresses constitutively in A. flavus. As a marker for transformation into C. nicotianae, the plasmid contains the bar gene, which encodes resistance to bialaphos. The plasmid is transformed into the mutant CS8 described above, and is shown to complement the cercosporin-sensitive mutation. The pyr4 gene, as described above, is then cloned into the plasmid construct in order to provide a marker for transformation into the Aspergillts strain 656-2. Transformants that exhibit resistance to cercosporin are then detected as described above.

EXAMPLE 5A

Expression of Resistance Genes in *Aspergillus flavus*

SOR1 was expressed in *Aspergillus flavus* according to the methods of Example 5 (expressing the SOR1 ORF downstream from the gpdA promoter). Data provided in Table 1 regarding gpdA:SOR1 transformants and three control colonies transformed only with vector, indicate that resistance of *A. flavus* to cercosporin can be improved by transformation with the SOR1 gene construct. A growth effect was also observed; the SOR1 transformants grew better in the absence of cercosporin. This effect may be due to the ability of SOR1 to complement a pyridoxine mutation. The particular *A. flavus* strain utilized was a pyridoxine mutant, however, all colonies were grown on complex media that contained pyridoxine.

TABLE 1

Growth of *A. flavus* gpdA:SOR1 transformants

| Strain | mm colony diameter 5 days (+10μM cercosporin) | mm colony diameter 5 days (no cercosporin) |
|---|---|---|
| SOR transformant #1 | 9 | 59 |
| SOR transformant #2 | 7 | 54 |
| SOR transformant #3 | 8 | 60 |
| Vector transformant #1 | 0 | 42 |
| Vector transformant #2 | 0 | 51 |
| Vector transformant #3 | 0 | 40 |

EXAMPLE 6

Isolation of Sor1 Homologue in *Alternaria alternata*

Figures 3A, 3B:
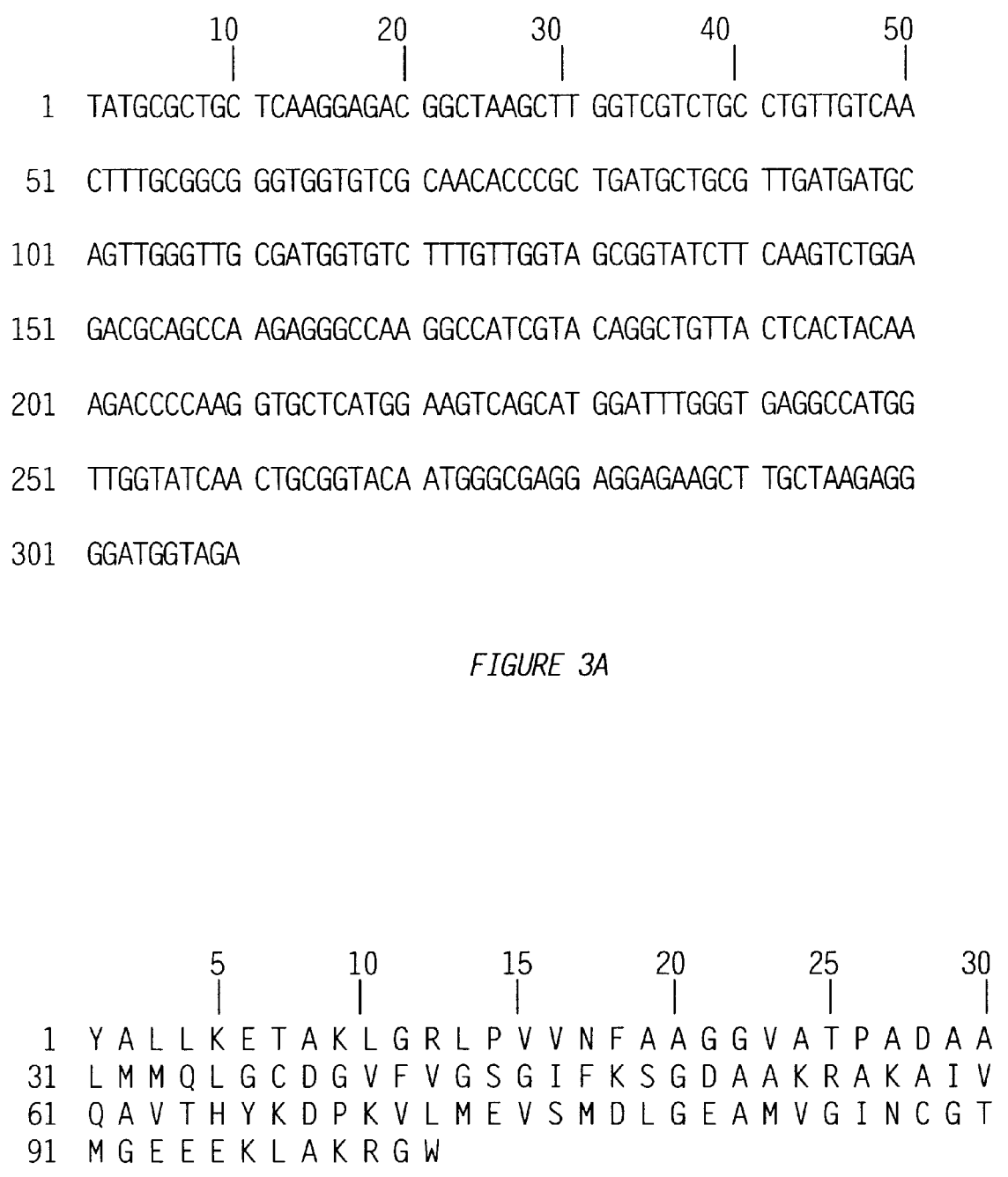

Using the *C. nicotianae* sor1 gene as a probe, a genomic library of the fungus *Alternaria alternata* was probed under conditions of lowered stringency, as defined above. A full-length *A. alternata* gene homologous to the *C. nicotianae* sor1 gene was isolated, and the gene sequenced according to known techniques (SEQ ID NO:10). A partial (310 base pairs) DNA sequence of the *A. alternata* gene is provided in FIG. 3A (SEQ ID NO:3); the predicted amino acid sequence, corresponding to the C-terminus of the protein encoded by the nucleic acid sequence, is provided in FIG. 3B (SEQ ID NO:4). The partial DNA sequence of the *A. alternata* gene is shown aligned with the corresponding segment of the *C. nicotianae* sor1 gene (SEQ ID NO:5) in FIG. 4A. In FIG. 4A, the "=" sign indicates that aligned residues are identical. Aligning the complete DNA sequences of the *A. alternata* gene (SEQ ID NO:10) and the *C. nicotianae sor*1 gene (SEQ ID NO:1) in a similar matter (not shown) indicates sequence identity of 78.2%.

The predicted C-terminus amino acid sequence of both genes is shown aligned in FIG. 4B (SEQ ID NO:6 (A. alternata) and SEQ ID NO:7 (SOR1)); the complete amino acid sequence of each gene (SEQ ID NO:2 and SEQ ID NO:11) is shown aligned in FIG. 4C. In FIGS. 4B and 4C, the "=" sign indicates that aligned residues are identical, while the "–" sign indicates that the aligned residues are similar. "Similar" residues are as follows: A, S, and T are deemed similar to each other; D and E are similar; N and Q are similar; R and K are similar; I, L, M and V are similar; and F, Y and W are similar.

The complete nucleotide sequence of the *A. alternata* homolog of SOR1 was sequenced (SEQ ID NO:10); the complete predicted amino acid sequence of the *A. alternata* homolog is provided in SEQ ID NO:11.

EXAMPLE 7

Determination of Homology to Other Known Genes and Gene Products

Protein sequences derived from the nucleotide sequence were analyzed for homology to other protein sequences using the National Center for Biotechnology Institute BLAST network service. S. F. Altshul et al. *J. Mol. Biol.* 215, 403–410 (1990)). The data base search revealed several protein sequences with 55–75% homology to the predicted polypeptide of SEQ ID NO:2, in organisms from divergent kingdoms, as shown in TABLE 2. There are no defined functions associated with any of the identified homologs. A yeast homologs encodes a protein that has been reported to increase in stationary phase; it has been suggested that this protein is a cell arrest protein (Braun et al., *J. Bacteriol.* 178:6865 (1996)). The gene from Hevea is up-regulated in the presence of ethylene and salicylic acid (Sivasubramaniam et al., *Plant Mol. Biol.* 29:173 (1995)).

TABLE 2

Presence of Homologues to SOR1

| Organism | Kingdom | Genome Sequence* | SOR1? |
|---|---|---|---|
| *Methanococcus jannaschii* | Archaebacteria | complete | Yes |
| *Methanococcus vaniellii* | | | Yes |
| *Pyrococcus furiosus* | | est | Yes |
| *Methanobacterium* thermoautotrophicum | | complete | Yes |
| *Archaeoglobus fulgidus* | | complete | Yes |
| *Haemophilus influenzae* | Eubacteria | complete | Yes |
| *Bacillus subtilis* | | complete | Yes |
| *Mycobacterium tuberculosis* | | not complete | Yes |
| *Mycobacterium leprae* | | | Yes |
| *Thermotoga maritima* | | not complete | Yes |
| *Deinococcus radiodurans* | | not complete | Yes |
| *Saccharomyces cerevisiae* | Fungi | complete | Yes/ 3 copies |
| *Schizosaccharomyces pombe* | | | Yes |
| *Aspergillus nidulans* | | est | Yes |
| *Caenorhabditis elegans* | Animal | not complete | Yes |
| *Arabidopsis* | Plant | est | Yes |
| Rice | Plant | est | Yes |
| *Stellaria longpipes* | Plant | | Yes |
| *Hevea brasiliensis* | Plant | expression library (ethylene) | Yes |

* complete = entire genome sequenced; not complete = genome sequencing underway but not complete; est = expressed sequence tags.

Organisms from the kingdom Eubacteria that lack SOR1 homologues have also been identified: *Escherichia coli*; Synechocysits; *Helicobacter pylori; Borrelia burgdoferi; Mycoplasina pneumoniae; Mycoplasma genitalium*. The complete genome has been sequenced for each of these organisms.

Many modifications and other embodiments of the invention will come to mind in one skilled in the art to which this invention pertains having the benefit of the teachings presented in the foregoing descriptions and the associated Figures. Therefore, it is to be understood that the invention is not to be limited to the specific embodiments disclosed. Although specific terms are employed, they are used in a generic and descriptive sense only and not for purposes of limitation. Modifications and alternative embodiments of the present invention are intended to be included within the scope of the appended claims.

EXAMPLE 8

Use of SOR1 as a Selectable Marker

SOR1 mutants were found to be unable to grow on minimal medium, but able to grow when the minimal medium was supplemented with pyridoxine. SOR1 does not show significant sequence similarity to any of the genes currently identified as acting in the pyridoxine biosynthetic pathway. SOR1 mutants were sensitive to cercosporin even when grown on medium containing pyridoxine, indicating that pyridoxine is not required for cercosporin resistance.

A pyridoxine-deficient mutant of *Aspergillus flavus* (ATCC#60045) was transformed using the protocol described in Example 5, above. Example 5 describes transformation and selection using the pyr4 gene, and selecting transformants based on the ability to grow without uridine. In the present experiment, protoplasts were transformed with constructs containing the SOR1 ORF under the control of the *Aspergillus niculans* glyceraldehyde-3-phosphate dehydrogenase gene (gpdA, promoter). The gpdA promoter is known to provide high, constitutive expression in *A. flavus*. Transformants were selected on minimal medium that lacked pyridoxine. Non-transformed protoplasts and protoplasts transformed with the vector plasmid lacking SOR1 did not grow; transformants expressing SOR1 grew. Transformation frequency appeared to be similar to that obtained with the pyr4 marker, although side-by-side comparisons have not been completed.

That which is claimed:

1. An isolated nucleic acid molecule which, when expressed in a cell, increases resistance in said cell to a photosensitizer, said molecule comprising a sequence selected from the group consisting of:
   (a) SEQ ID NO:1;
   (b) nucleotides 825–1853 of SEQ ID NO:1;
   (c) sequences that encode, a polypeptide comprising the amino acid sequence of SEQ ID NO:2; and
   (d) sequences that hybridize to a sequence of (a), (b) or (c), above under strinegent conditions represented by a wash stringency of 50% Formanide with 5× Denhardt's solution, 0.5% SDS and 1× SSPE at 42° C., and that, when expressed in a cell, increase resistance in said cell to a photosensitizer.

2. An isolated nucleic acid molecule according to claim 1, wherein said photosensitizer produces singlet oxygen upon the reaction of said photosensitizer with light and oxygen.

3. An isolated nucleic acid molecule according to claim 1, wherein said photosensitizer is cercosporin.

4. An isolated nucleic acid according to claim 1, wherein said cell is a fungal cell.

5. An isolated nucleic acid molecule according to claim 1, wherein said cell is a plant cell.

6. A transformed cell comprising a chimeric gene, said gene comprising a nucleotide sequence according to claim 1 operably linked with a promoter.

7. A transformed cell according to claim 6, wherein said cell is a plant cell.

8. A method for increasing resistance to a photosensitizer in a cell, comprising transforming said cell with an nucleic acid molecule of claim 1.

9. A method for increasing resistance to a photosensitizer in a cell according to claim 8, wherein said photosensitizer produces singlet oxygen upon the reaction of said photosensitizer with light and oxygen.

10. A method for increasing resistance to a photosensitizer in a cell according to claim 8, wherein said photosensitizer is cercosporin.

11. A method according to claim 10, wherein said cell is a plant cell.

12. A method of increasing resistance in a cell to a pathogen, wherein the pathogen produces a photosensitizer, the method comprising transforming said cell with an isolated nucleic acid molecule of claim 1.

13. A method according to claim 12, wherein said photosensitizer is cercosporin.

14. A method according to claim 12, wherein said pathogen is a fungus.

15. A method according to claim 14, wherein said pathogen is selected from the group consisting of the Cercospora species.

16. A method of increasing resistance in an cell to singlet oxygen, comprising transforming said cell with an isolated nucleic acid molecule of claim 1.

17. An expression cassette comprising a chimeric gene, said gene comprising a nucleotide sequence according to claim 1 operably linked with a promoter.

18. A transformed plant comprising a chimeric gene, said gene comprising a nucleotide sequence according to claim 1 operably linked with a promoter.

19. A transformed plant comprising an expression cassette according to claim 17.

20. A method for increasing resistance to a photosensitizer in a plant, comprising transforming said plant with an expression cassette according to claim 17.

21. A method according to claim 20, wherein said photosensitizer is cercosporin.

22. A method according to claim 20, wherein said plant is selected from the group consisting of rape, canola, sorghum, soybean, sugar beet, corn and tobacco.

23. A method for increasing resistance to infection by a fungal pathogen in a plant, wherein said fungal pathogen produces a photosensitizer, the method comprising transforming said plant with an expression cassette according to claim 20.

24. A method according to claim 23, wherein said fungal pathogen is selected from the group consisting of the Cercospora species.

25. A method according to claim 23, wherein said plant is selected from the group consisting of rape, canola, sorghum, soybean, sugar beet, corn and tobacco.

26. An isolated nucleic acid molecule which, when expressed in a cell, increases resistance in said cell to a photosensitizer, said molecule comprising a sequence selected from the group consisting of:

(a) SEQ ID NO:8;

(b) nucleotides 742–2391 of SEQ ID NO:8;

(c) sequences that encode a polypeptide comprising the amino acid sequence of SEQ ID NO:9; and (d) sequences that hybridize to a sequence of (a), (b) or (c), above under stringent conditions represented by a wash stringency of 50% Formamide with 5× Denhardt's solution, 0.5% SDS and 1× SSPE at 42° C., and that, when expressed in a cell, increase resistance in said cell to a photosensitizer.

27. An isolated nucleic acid according to claim 26, wherein said cell is a fungal cell or a plant cell.

28. A transformed cell comprising a chimeric gene, said gene comprising a nucleotide sequence according to claim 26 operably linked with a promoter.

29. A transformed cell according to claim 28, wherein said cell is a plant cell.

30. A method for increasing resistance to cercosporin in a cell, comprising transforming said cell with an nucleic acid molecule of claim 26.

31. A method according to claim 30, wherein said cell is a plant cell.

32. A method of increasing resistance in a cell to a pathogen, wherein the pathogen produces cercosporin, the method comprising transforming said cell with an isolated nucleic acid molecule of claim 26.

33. A method according to claim 32, wherein said pathogen is a fungus.

34. A method according to claim 33, wherein said pathogen is selected from the group consisting of the Cercospora species.

35. An expression cassette comprising a chimeric gene, said gene comprising a nucleotide sequence according to claim 26 operably linked with a promoter.

36. A transformed plant comprising a chimeric gene, said gene comprising a nucleotide sequence according to claim 26 operably linked with a promoter.

37. A transformed plant comprising an expression cassette according to claim 35.

38. A method for increasing resistance to cercosporin in a plant, comprising transforming said plant with an expression cassette according to claim 35.

39. A method according to claim 38, wherein said plant is selected from the group consisting of rape, canola, sorghum, soybean, sugar beet, corn and tobacco.

40. A method for increasing resistance to infection by a fungal pathogen in a plant, wherein said fungal pathogen produces cercosporin, the method comprising transforming said plant with an expression cassette according to claim 35.

41. A method according to claim 40, wherein said fungal pathogen is selected from the group consisting of the Cercospora species.

42. A method according to claim 40, wherein said plant is selected from the group consisting of rape, canola, sorghum, soybean, sugar beet, corn and tobacco.

* * * * *

UNITED STATES PATENT AND TRADEMARK OFFICE
CERTIFICATE OF CORRECTION

PATENT NO. : 6,063,987  
DATED : May 16, 2000  
INVENTOR(S) : Daub et al.

Page 1 of 1

It is certified that error appears in the above-identified patent and that said Letters Patent is hereby corrected as shown below:

<u>Title page,</u>  
Item [63], Related U.S. Application Data, the following Related U.S. Application Data should be added:  
-- Provisional application No. 60,040,615 filed 03/17/1997, now abandoned. --

<u>Column 10,</u>  
Line 43, should read:  
-- 89:245-254; Uknes et al. (1992) *The Plant Cell* 4:645-656; and Van Loon (1985) *Plant Mol. Virol.* 4:111-116. --

<u>Column 42,</u>  
Line 8, should read:  
-- method comprising transforming said cell with an isolated --

Signed and Sealed this

Twentieth Day of August, 2002

Attest:

Attesting Officer

JAMES E. ROGAN  
*Director of the United States Patent and Trademark Office*